(12) United States Patent
Richter et al.

(10) Patent No.: US 11,534,194 B2
(45) Date of Patent: Dec. 27, 2022

(54) TOOLS AND METHODS FOR TISSUE REMOVAL

(71) Applicant: DePuy Synthes Products, Inc., Raynham, MA (US)

(72) Inventors: Jörn Richter, Kandern (DE); Salman Chegini, Bern (CH); Daniel Thommen, Liestal (CH)

(73) Assignee: DePuy Synthes Products, Inc., Raynham, MA (US)

( * ) Notice: Subject to any disclaimer, the term of this patent is extended or adjusted under 35 U.S.C. 154(b) by 222 days.

(21) Appl. No.: 16/812,857

(22) Filed: Mar. 9, 2020

(65) Prior Publication Data
US 2020/0275946 A1 Sep. 3, 2020

Related U.S. Application Data

(63) Continuation of application No. 15/470,236, filed on Mar. 27, 2017, now Pat. No. 10,582,943, which is a
(Continued)

(51) Int. Cl.
*A61B 17/32* (2006.01)
*A61B 17/16* (2006.01)
(Continued)

(52) U.S. Cl.
CPC .... *A61B 17/32002* (2013.01); *A61B 17/1615* (2013.01); *A61B 17/1617* (2013.01); *A61B 17/1633* (2013.01); *A61B 17/1659* (2013.01); *A61B 17/1671* (2013.01); *A61B 17/320725* (2013.01); *A61B 2017/00261* (2013.01);
(Continued)

(58) Field of Classification Search
CPC ..................... A61B 17/1671; A61B 17/32002
See application file for complete search history.

(56) References Cited

U.S. PATENT DOCUMENTS

| 4,857,046 A | 8/1989 | Stevens et al. |
| 5,248,297 A | 9/1993 | Takase |

(Continued)

FOREIGN PATENT DOCUMENTS

| CN | 102458274 | 5/2012 |
| FR | 2714285 | 6/1995 |

(Continued)

OTHER PUBLICATIONS

International Preliminary Report on Patentability and Written Opinion, dated Sep. 15, 2015, received in connection with International Patent Publication No. PCT/US2014/021252.
(Continued)

*Primary Examiner* — Olivia C Chang
(74) *Attorney, Agent, or Firm* — Meunier Carlin & Curfman LLC

(57) ABSTRACT

The present invention is directed to material removal instrument for forming cavities in interior body regions, particularly cavities in intervertebral discs and vertebrae. The instrument includes a cannula and a rotation mechanism disposed at least partially within the cannula. A cutting element extends from the rotation mechanism and impacts and dislocates tissue as the rotation mechanism is rotated within the body. Dislocated tissue with withdrawn from the body via the cannula.

20 Claims, 34 Drawing Sheets

Related U.S. Application Data continuation of application No. 13/836,889, filed on Mar. 15, 2013, now Pat. No. 9,603,610.

(51) Int. Cl.
  *A61B 17/3207* (2006.01)
  *A61B 17/00* (2006.01)

(52) U.S. Cl.
  CPC .............. *A61B 2017/00685* (2013.01); *A61B 2017/320024* (2013.01); *A61B 2017/320733* (2013.01); *A61B 2017/320766* (2013.01)

(56) References Cited

U.S. PATENT DOCUMENTS

| | | | |
|---|---|---|---|
| 5,285,795 A | 2/1994 | Ryan et al. | |
| 5,383,884 A | 1/1995 | Summers | |
| 5,395,317 A | 3/1995 | Kambin | |
| 5,591,187 A | 1/1997 | Dekel | |
| 5,620,447 A | 4/1997 | Smith et al. | |
| 5,685,840 A | 11/1997 | Schechter et al. | |
| 5,752,969 A | 5/1998 | Cunci et al. | |
| 5,755,731 A | 5/1998 | Grinberg | |
| 5,961,532 A | 10/1999 | Finley et al. | |
| 5,976,105 A | 11/1999 | Marcove et al. | |
| 6,083,237 A | 7/2000 | Huitema et al. | |
| 6,200,322 B1 | 3/2001 | Branch et al. | |
| 6,296,639 B1 | 10/2001 | Truckai et al. | |
| 6,332,894 B1 | 12/2001 | Stalcup et al. | |
| 6,464,711 B1 | 10/2002 | Emans et al. | |
| 6,533,749 B1 | 3/2003 | Mitusina et al. | |
| 6,620,180 B1 | 9/2003 | Bays et al. | |
| 6,663,626 B2 | 12/2003 | Truckai et al. | |
| 6,679,886 B2 | 1/2004 | Weikel et al. | |
| 6,733,496 B2 | 5/2004 | Sharkey et al. | |
| 6,746,451 B2 | 6/2004 | Middleton et al. | |
| 6,805,697 B1 | 10/2004 | Helm et al. | |
| 6,821,276 B2 | 11/2004 | Lambrecht et al. | |
| 7,322,962 B2 | 1/2008 | Forrest | |
| 7,338,495 B2 | 3/2008 | Adams | |
| 7,500,977 B2 | 3/2009 | Assell et al. | |
| 7,632,294 B2 | 12/2009 | Milbodker et al. | |
| 7,731,719 B2 | 6/2010 | Nordt | |
| 7,803,159 B2 | 9/2010 | Perez-Cruet et al. | |
| 7,803,170 B2 | 9/2010 | Mitusina | |
| 7,905,863 B1 | 3/2011 | Forrest | |
| 7,927,361 B2 | 4/2011 | Oliver et al. | |
| 7,959,634 B2 | 6/2011 | Sennett | |
| 8,048,081 B2 | 11/2011 | Shaolian et al. | |
| 8,052,613 B2 | 11/2011 | Assell et al. | |
| 8,109,957 B2 | 2/2012 | Stad et al. | |
| 8,118,845 B2 | 2/2012 | White | |
| 8,123,750 B2 | 2/2012 | Norton et al. | |
| 8,221,425 B2 | 7/2012 | Arcenio et al. | |
| 8,246,622 B2 | 8/2012 | Siegal et al. | |
| 8,277,474 B2 | 10/2012 | Norman et al. | |
| 8,282,661 B2 | 10/2012 | Eckman | |
| 8,328,812 B2 | 12/2012 | Siegal et al. | |
| 2002/0138091 A1 | 9/2002 | Pflueger | |
| 2002/0147497 A1 | 10/2002 | Belef et al. | |
| 2002/0183758 A1* | 12/2002 | Middleton ......... A61B 17/1671 606/80 |
| 2003/0191474 A1 | 10/2003 | Cragg et al. | |
| 2004/0138673 A1 | 7/2004 | Lambrecht et al. | |
| 2005/0149034 A1 | 7/2005 | Assell et al. | |
| 2005/0203527 A1 | 9/2005 | Carrison et al. | |
| 2005/0209530 A1 | 9/2005 | Pflueger | |
| 2005/0209610 A1 | 9/2005 | Carrison | |
| 2006/0095045 A1 | 5/2006 | Trieu | |
| 2006/0095046 A1 | 5/2006 | Trieu et al. | |
| 2006/0106410 A1 | 5/2006 | Serhan et al. | |
| 2006/0135959 A1 | 6/2006 | Yuan et al. | |
| 2006/0149268 A1 | 6/2006 | Truckai et al. | |
| 2006/0206127 A1 | 9/2006 | Conquergood et al. | |
| 2006/0241566 A1 | 10/2006 | Moon et al. | |
| 2006/0264957 A1 | 11/2006 | Cragg et al. | |
| 2007/0149975 A1 | 6/2007 | Oliver et al. | |
| 2007/0213584 A1 | 9/2007 | Kim et al. | |
| 2007/0255172 A1 | 11/2007 | Pflueger | |
| 2007/0265633 A1 | 11/2007 | Moon et al. | |
| 2008/0084157 A1 | 4/2008 | Takahashi et al. | |
| 2009/0088848 A1 | 4/2009 | Martz et al. | |
| 2009/0143809 A1 | 6/2009 | Assell et al. | |
| 2009/0209989 A1 | 8/2009 | Blake et al. | |
| 2009/0264939 A9 | 10/2009 | Martz et al. | |
| 2009/0292361 A1 | 11/2009 | Lopez | |
| 2010/0030216 A1 | 2/2010 | Arcenio | |
| 2010/0076479 A1 | 3/2010 | Monstadt | |
| 2010/0286782 A1 | 11/2010 | Schaller et al. | |
| 2010/0292700 A1 | 11/2010 | Ries | |
| 2011/0054507 A1 | 3/2011 | Batten et al. | |
| 2011/0112563 A1 | 5/2011 | To et al. | |
| 2011/0166576 A1 | 7/2011 | Oliver et al. | |
| 2011/0166603 A1 | 7/2011 | Forrest | |
| 2011/0190803 A1 | 8/2011 | To et al. | |
| 2011/0208253 A1 | 8/2011 | Milijasevic et al. | |
| 2011/0295272 A1 | 12/2011 | Assell et al. | |
| 2011/0313529 A1 | 12/2011 | Schaller et al. | |
| 2012/0071880 A1 | 3/2012 | Suddaby | |
| 2012/0101513 A1 | 4/2012 | Shadeck et al. | |
| 2012/0179183 A1 | 7/2012 | Stad et al. | |
| 2012/0197279 A1 | 8/2012 | Perez-Cruet et al. | |
| 2012/0197280 A1 | 8/2012 | Emanuel | |
| 2012/0209273 A1 | 8/2012 | Zaretzka et al. | |
| 2012/0271313 A1 | 10/2012 | Lauchner | |
| 2012/0271357 A1 | 10/2012 | Arthur et al. | |
| 2012/0283742 A1 | 11/2012 | Dubois et al. | |
| 2013/0018376 A1 | 1/2013 | Yoon et al. | |
| 2013/0018377 A1 | 1/2013 | Williams | |
| 2013/0023882 A1 | 1/2013 | Fabro et al. | |
| 2014/0180321 A1 | 6/2014 | Dias et al. | |

FOREIGN PATENT DOCUMENTS

| | | |
|---|---|---|
| JP | 2005-510259 | 4/2005 |
| JP | 2011-528962 | 12/2011 |
| WO | 2012/037137 | 3/2012 |
| WO | 2012/112597 | 8/2012 |
| WO | 2013/009986 | 1/2013 |
| WO | 2013/016698 | 1/2013 |

OTHER PUBLICATIONS

International Search Report, dated Aug. 4, 2014, received in connection with International Patent Publication No. PCT/US2014/021252.

\* cited by examiner

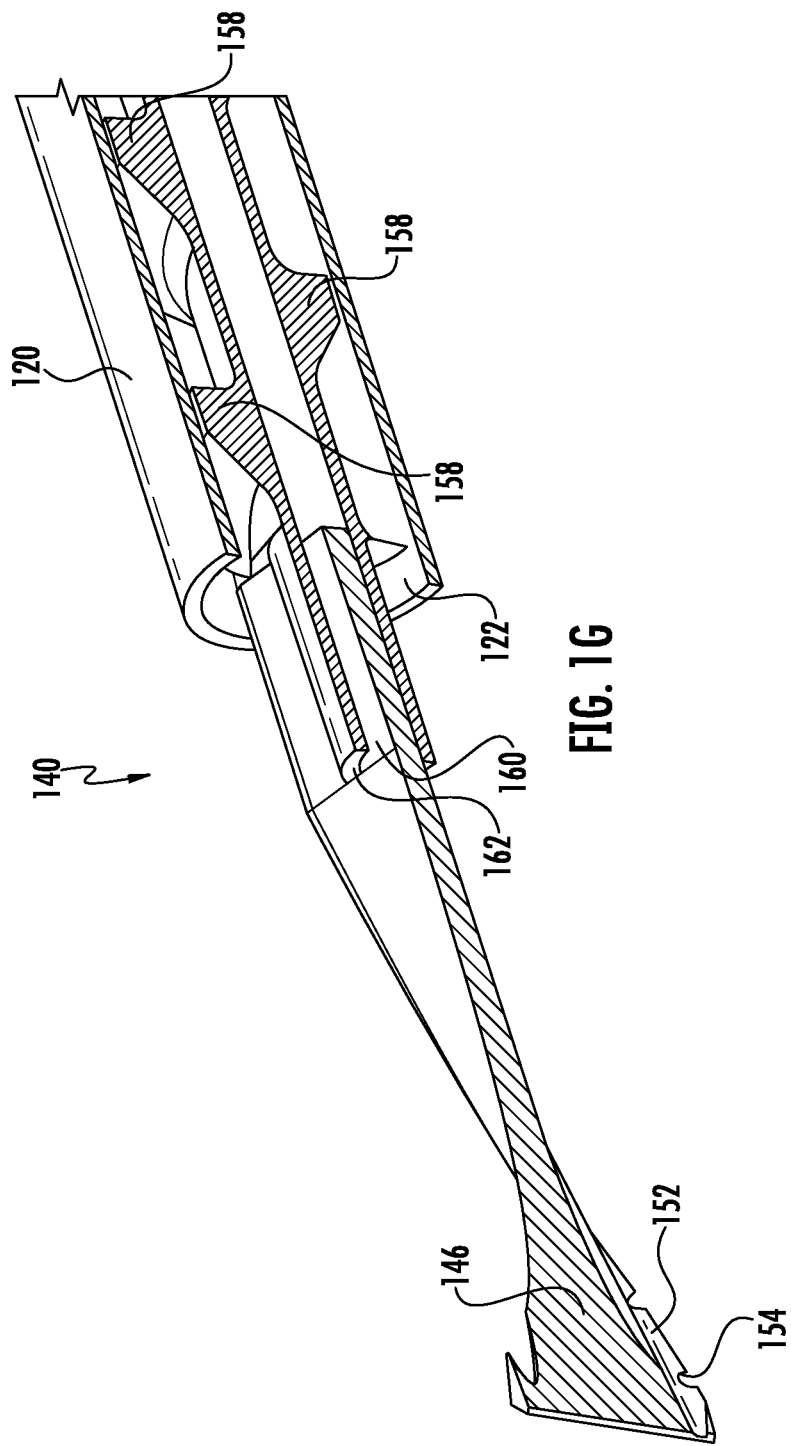

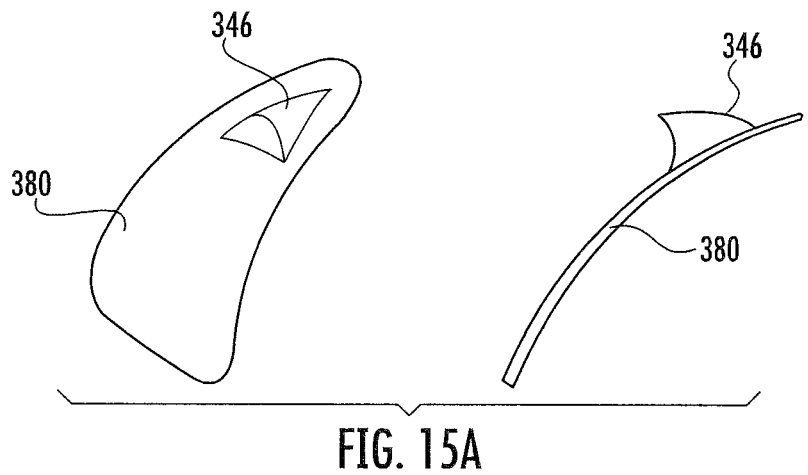
FIG. 15A
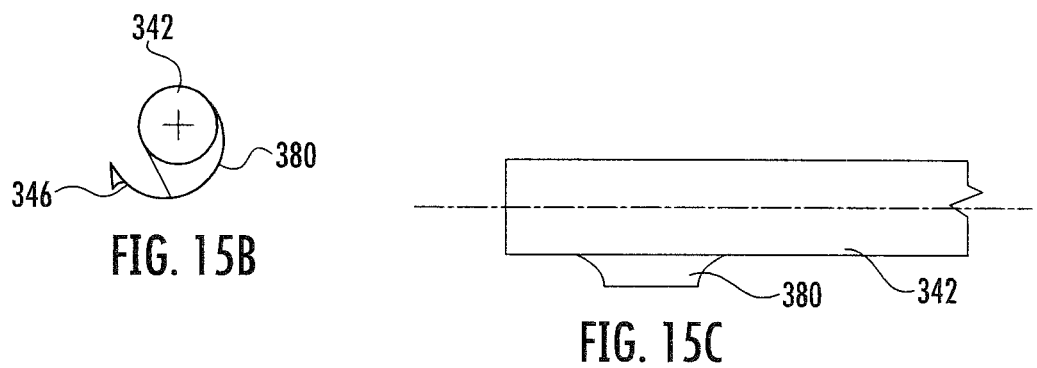
FIG. 15B
FIG. 15C
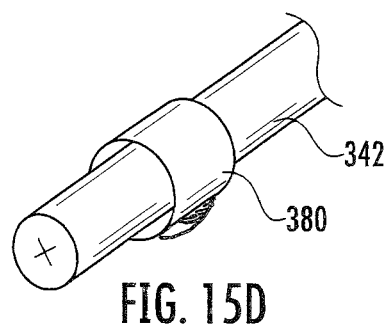
FIG. 15D

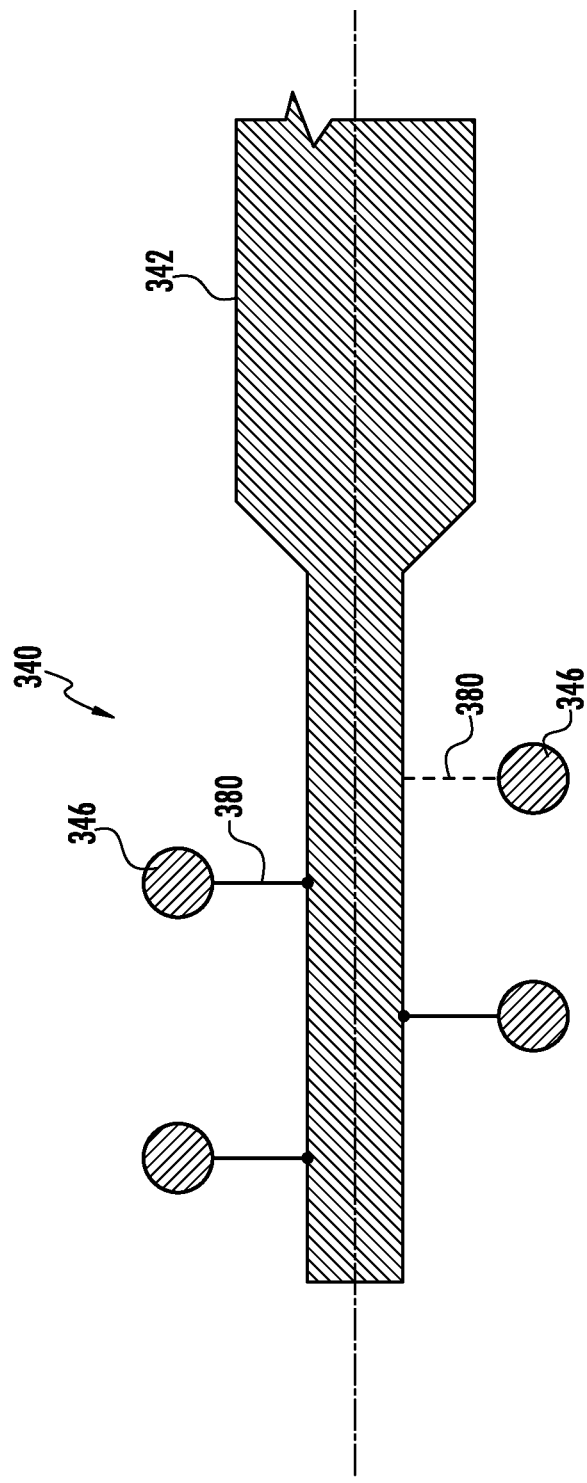

TOOLS AND METHODS FOR TISSUE REMOVAL

CROSS-REFERENCE TO RELATED APPLICATIONS

This application is a continuation of U.S. application Ser. No. 15/470,236 (issued as U.S. Pat. No. 10,582,943), filed Mar. 27, 2017, entitled "Tools and Methods for Tissue Removal," which is a continuation of U.S. application Ser. No. 13/836,889 (issued as U.S. Pat. No. 9,603,610), filed Mar. 15, 2013, entitled "Tools and Methods for Tissue Removal," the disclosures of which are hereby incorporated by reference.

TECHNICAL FIELD

This invention relates generally to tools and procedures for forming cavities in interior body regions, particularly in intervertebral discs and vertebrae, for diagnostic and therapeutic purposes.

BACKGROUND

Certain diagnostic and therapeutic procedures for treatment and removal of disc material require access to and/or formation of a cavity in an interior body region, including the intervertebral disc. The intervertebral disc includes a thick outer ring of elastic soft tissue material (annulus fibrosus) and an inner gel-like substance (nucleus pulposus). Healthy disc material helps maintain flexibility of the spine and acts as a shock absorber dissipating loads across the spine. When the condition of the disc material deteriorates as a result of, for example, degenerative disc disease, herniation, and/or injury, the patient may suffer deformation of the normal alignment or curvature of the affected area of the spine, as well as chronic complications and an overall adverse impact upon the quality of life.

Until recently, doctors were limited to treating such deterioration and related deformities with pain medications, bed rest, bracing or invasive spinal surgery. Surgical removal of the offending disc material can be completed (e.g., discectomy) to provide a treatment element to the disc space (e.g., bone graft, filler material, etc.) and/or fusion of adjacent vertebral bodies using metal screws/rods. Standard surgical instruments for removing and/or creating a cavity in the intervertebral disc include chisels, disc cutters, rasps, pituitary rongeurs, scrapers, curettes, cobb elevators, sizers, broaches or the like. The surgical procedure for accessing the disc may depend upon patient anatomy and/or disc/vertebral condition.

A common drawback of most systems for removing disc material is that they require significant dissection and muscle retraction to accommodate the multitude tools needed for creating the cavity, leading to longer recovery time for the patient. Accordingly, there remains a need in the art to provide a safe and effective apparatus and method for minimally invasive disc tissue detachment and removal.

SUMMARY

The present invention is directed to tools and methods for creating cavities in a body, in particular, cavities in intervertebral disc material and cancellous bone. An aspect of the present disclosure is directed to a material removal instrument. The material removal instrument may include a cannula and a rotation mechanism. The cannula may include a cannula bore and a cannula opening at a distal end of the cannula, where the cannula opening can provide access to the cannula bore. All or a portion of the cannula may be constructed from a rigid or flexible material. Flexibility can be achieved based on the material properties of the cannula, structural properties and/or modifications to the cannula, and/or a linkage with another portion of the material removal instrument. The rotation mechanism may be disposed at least partially within the cannula. The rotation mechanism may include an elongated shaft having a central bore and an opening at a distal end of the elongated shaft providing access to the central bore. The central bore of the elongated shaft may be used to provide irrigation to the cutting area. The central bore of the elongated shaft may be sized and configured to receive a guide wire to direct placement of the rotation mechanism. All or a portion of the rotation mechanism, including the elongated shaft, may be constructed from a rigid or flexible material. Flexibility can be achieved based on the material properties of the rotation mechanism/elongated shaft, structural properties and/or modifications to the rotation mechanism/elongated shaft, and/or a linkage with another portion of the material removal instrument. Flexibility of the cannula and/or the rotation mechanism can be used to provide steering/directional control when accessing the target area and during removal of tissue. The elongated shaft may also include a central bore In one aspect, the rotation mechanism may also include projections extending from a portion of the elongated shaft and a blade extending from an other portion of the elongated shaft. The blade may be used for dislocating material from a target area. At least a portion of the blade may extend from the cannula opening. The rotation mechanism may be rotated within the cannula to cause the blade to dislocate material from the target area. The dislocated material may be drawn from the target area through the cannula bore.

Another aspect of the present disclosure is directed to a material removal instrument that may include a cannula and a rotation mechanism. The cannula may include a cannula bore and a cannula opening at a distal end of the cannula. The cannula opening may provide access to the cannula bore. The rotation mechanism may be disposed at least partially within the cannula. The rotation mechanism may include an elongated shaft and a thread extending from a portion of the elongated shaft. The thread may be used for dislocating material from a target area. The thread may include a flank having a leading side and a trailing side. The trailing side may have a flank angle less than 90° with respect to a longitudinal axis of the rotation mechanism. At least a portion of the rotation mechanism may extend from the cannula opening. The rotation mechanism may be rotated within the cannula to cause the thread to impact and dislocate material from the target area.

A further aspect of the present disclosure is directed to a material removal instrument that may include a cannula and a rotation mechanism. The cannula may include a cannula bore and a cannula opening at a distal end of the cannula. The cannula opening may provide access to the cannula bore. The rotation mechanism may be disposed at least partially within and rotatable within the cannula. The rotation mechanism may include an elongated shaft, a connection element, and a mass element. The connection element may be fixed to the elongated shaft. The mass element may be used for dislocating material from a target area. The mass element may be fixed to the connection element. Rotation of the rotation mechanism may cause the connection element to move in a direction away from a longitudinal axis of the rotation mechanism. Rotation of the rotation mechanism may also cause the mass element to rotate about the longitudinal axis of the rotation mechanism at a distance from the longitudinal axis. Rotation of the mass element may cause the mass element to impact and dislocate material from the target area.

Another aspect of the present disclosure is directed to a material removal instrument that may include a cannula and a cutting element. The cannula may include a cannula bore and a cannula opening at a distal end of the cannula. The cannula opening may provide access to the cannula bore. The cutting element may be disposed at least partially within the cannula and attached to an inner element. The cutting element may expand radially from the cannula opening upon movement of the inner element from a first position to a second position in a direction along a longitudinal axis of the cannula. The rotation of the cannula with the cutting element in the expanded position may cause the cutting element to impact and dislocate material from a target area.

The details of one or more embodiments of the invention are set forth in the accompanying drawings and the description below. Other features, objects, and advantages of the invention will be apparent from the description and drawings, and from the claims.

DESCRIPTION OF DRAWINGS

The device is explained in even greater detail in the following drawings. The drawings are merely examples to illustrate the structure of preferred devices and certain features that may be used singularly or in combination with other features. The invention should not be limited to the examples shown.

FIG. 1G is a partial cross-section view of an example material removal instrument;

FIG. 15A is a perspective view of an example connection element and mass element;

FIG. 15B is a partial end view of an example rotation mechanism;

FIG. 15C is a partial side view of an example rotation mechanism;

FIG. 15D is a partial perspective view of an example rotation mechanism;

FIG. 16A is a partial side view of an example rotation mechanism;

Like reference symbols in the various drawings indicate like elements.

DETAILED DESCRIPTION

Figure 1A:
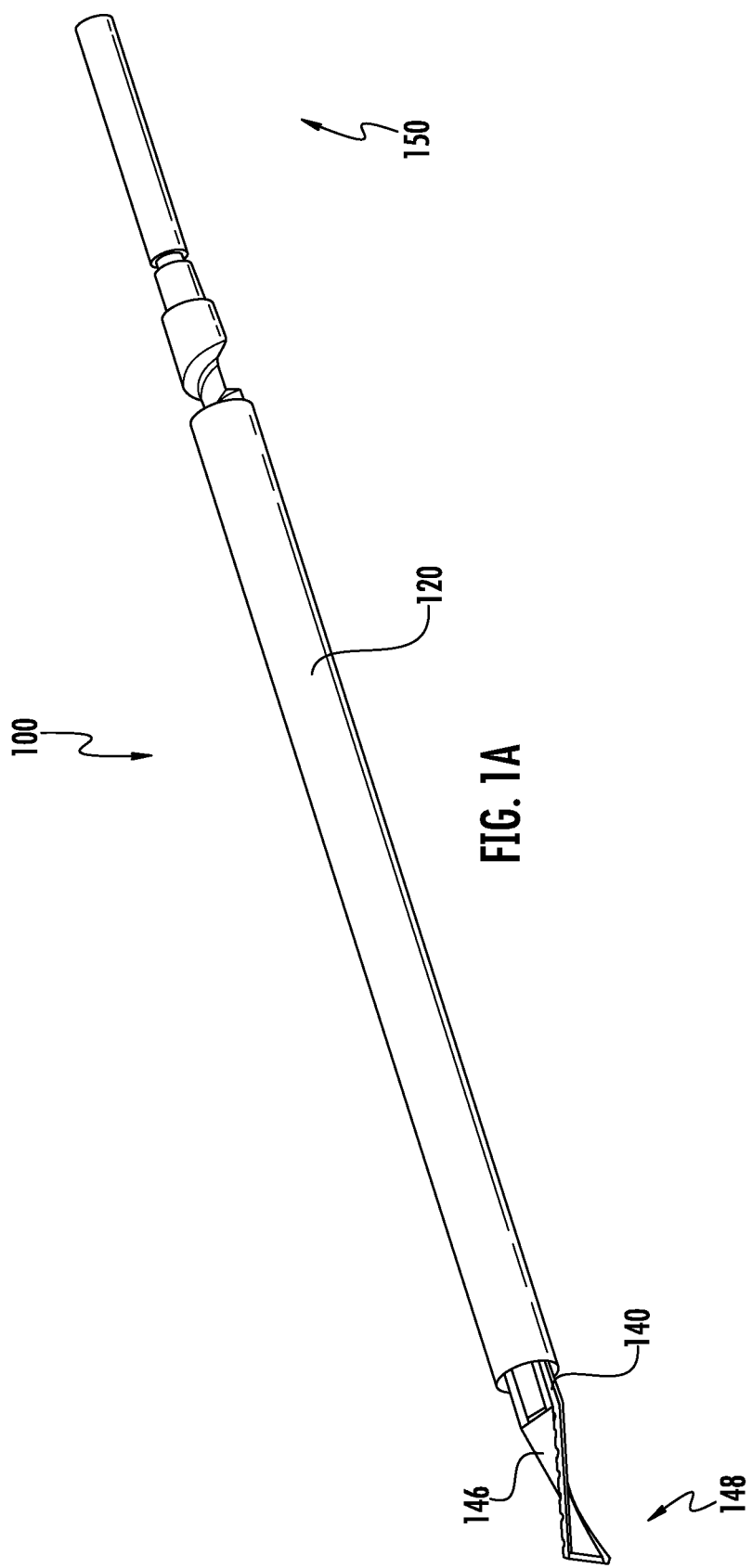
FIG. 1A is a perspective view of an example material removal instrument.
Figure 1B:
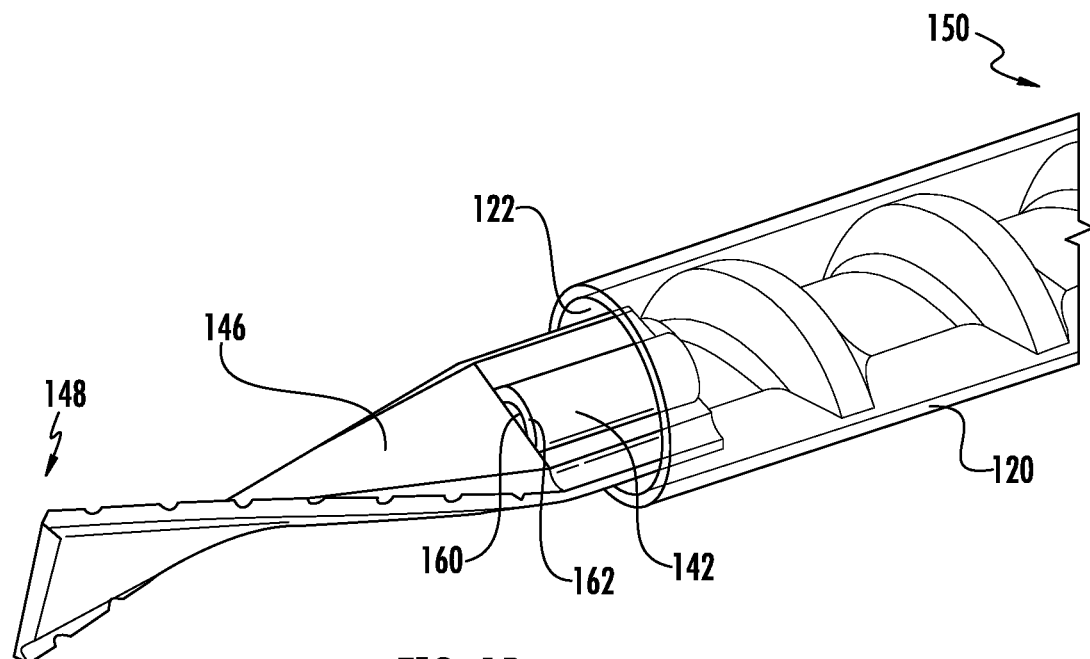
FIG. 1B is a partial perspective view of an example material removal instrument.
Figure 1C:
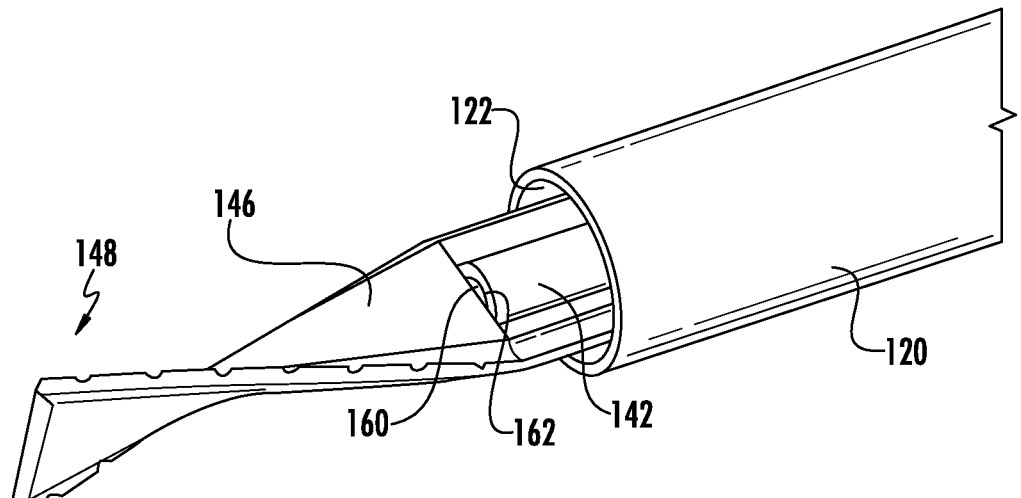
FIG. 1C is a partial perspective view of an example material removal instrument.
Figure 1D:
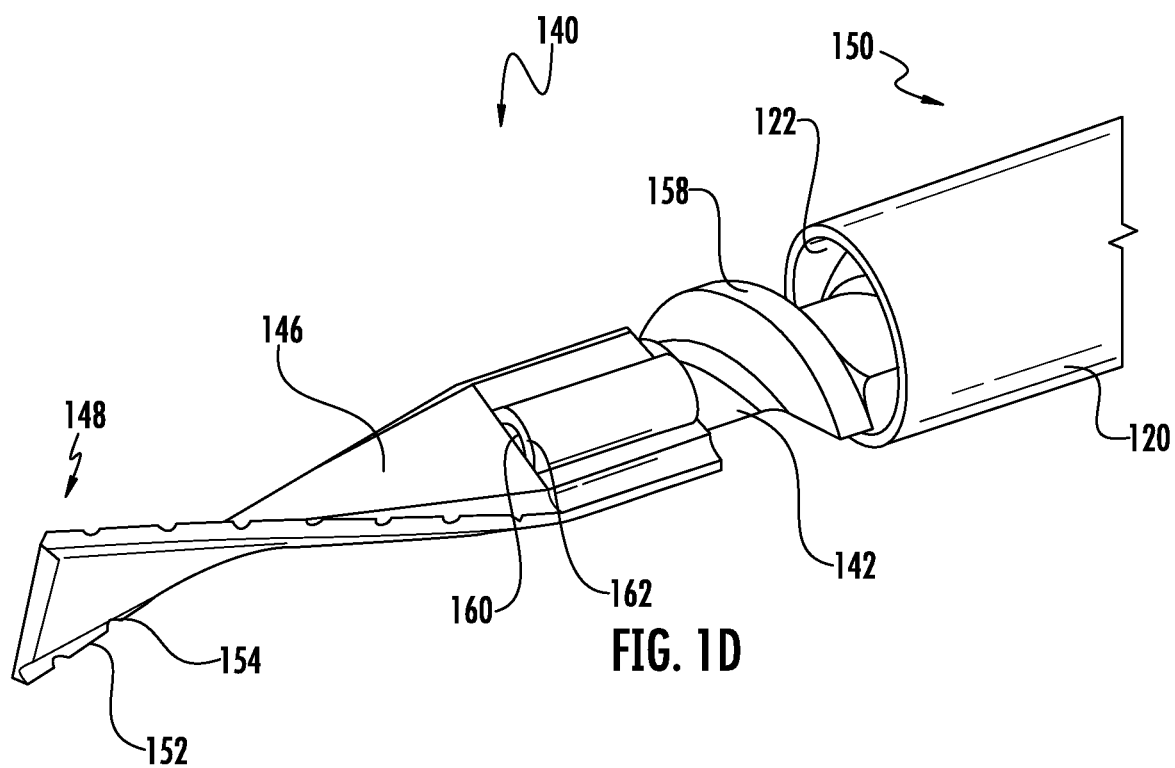
FIG. 1D is a partial perspective view of an example material removal instrument.
Figure 1E:
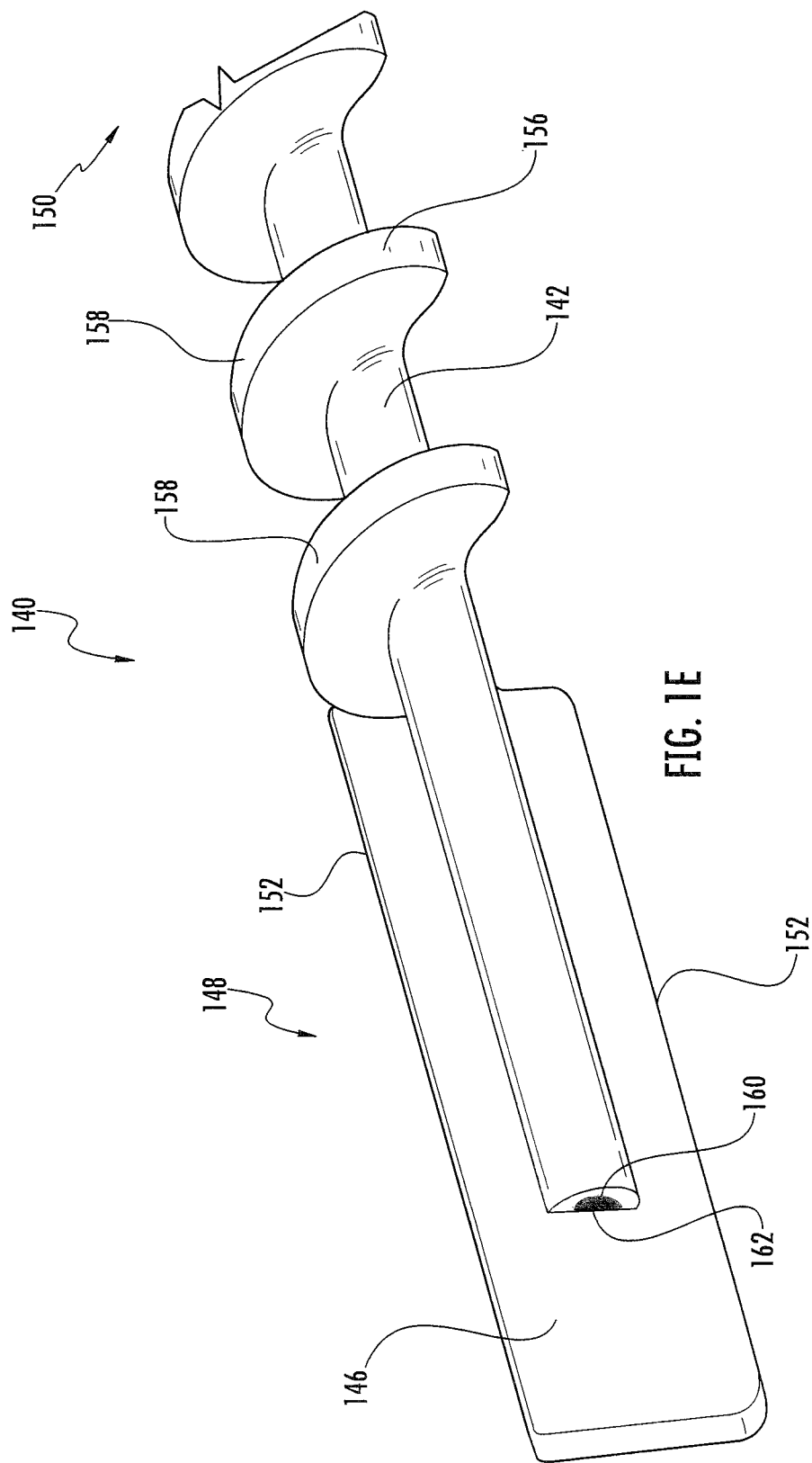
FIG. 1E is a partial perspective view of an example material removal instrument.
Figure 1F:
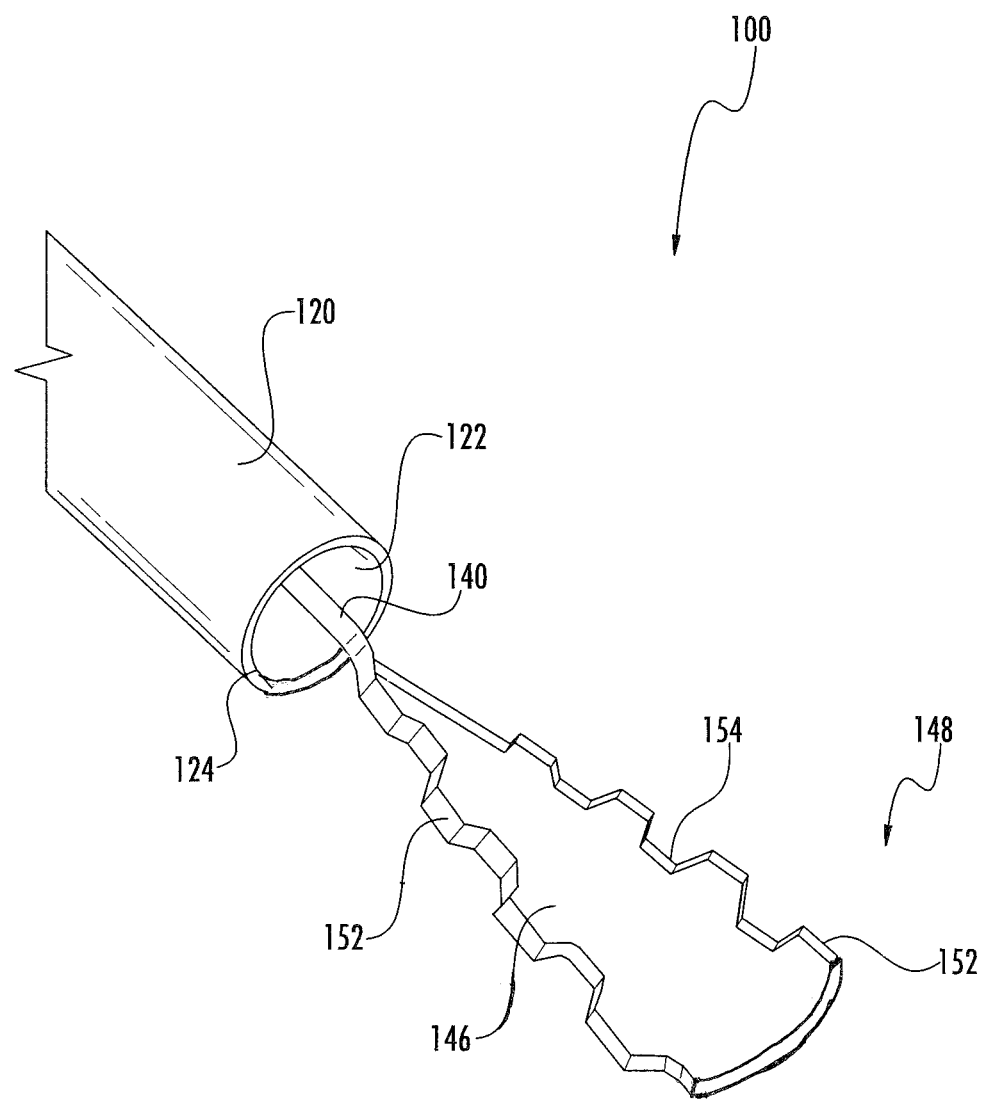
FIG. 1F is a partial perspective view of an example material removal instrument.

Certain terminology is used in the following description for convenience only and is not limiting. The words "right", "left", "lower", and "upper" designate direction in the drawings to which reference is made. The words "inner", "outer" refer to directions toward and away from, respectively, the geometric center of the described feature or device. The words "distal" and "proximal" refer to directions taken in context of the item described and, with regard to the instruments herein described, are typically based on the perspective of the surgeon using such instruments. The words "anterior", "posterior", "superior", "inferior", "medial", "lateral", and related words and/or phrases designate preferred positions and orientation in the human body to which reference is made. The terminology includes the above-listed words, derivatives thereof, and words of similar import.

In addition, various components may be described herein as extending horizontally along a longitudinal direction "L" and lateral direction "A", and vertically along a transverse direction "T". Unless otherwise specified herein, the terms "lateral", "longitudinal", and "transverse" are used to describe the orthogonal directional components of various items. It should be appreciated that while the longitudinal and lateral directions are illustrated as extending along a horizontal plane, and that the transverse direction is illustrated as extending along a vertical plane, the planes that encompass the various directions may differ during use. Accordingly, the directional terms "vertical" and "horizontal" are used to describe the components merely for the purposes of clarity and illustration and are not meant to be limiting Certain examples of the invention will now be described with reference to the drawings. In general, such embodiments relate to a material removal instrument for cavities in intervertebral disc material and cancellous bone.

FIGS. 1A-1G provide perspective views of example material removal instruments 100. The example material removal instrument 100 can include a cannula 120 and a rotation mechanism 140. The rotation mechanism 140 can include a shaft 142. The shaft 142 can define an elongated cylindrical structure. In another example (not shown), the shaft 142 can define an elongated structure with a cross-section having any suitable shape including, for example, elliptical, square, rectangular, or any other regular or irregular shape. The shaft 142 can be constructed from a flexible material (e.g., polymers, Nitinol) or a rigid material. An example shaft 142 constructed from a stiff and/or rigid material can include structural modification (e.g., geometric cutouts or shapes) that provide an overall flexible behavior regarding cross forces. The flexibility of the shaft 142 can also be achieved by a linkage (not shown) between the cutting surface 152 and the flanks 158.

The shaft 142 can include a blade 146 extending from the outer surface of the shaft 142 body. The blade 146 can extend in a radial direction from the outer surface of the shaft 142 along a length of the shaft 142 in the longitudinal direction. Likewise, the blade 146 can extend from the distal end 148 of the shaft 142. An example blade 146 can have a length along the longitudinal axis of the shaft 142 of about 12 mm to about 17 mm. An example blade 146 can have a thickness ranging from about 0.4 mm to about 2 mm.

Figure 2A:
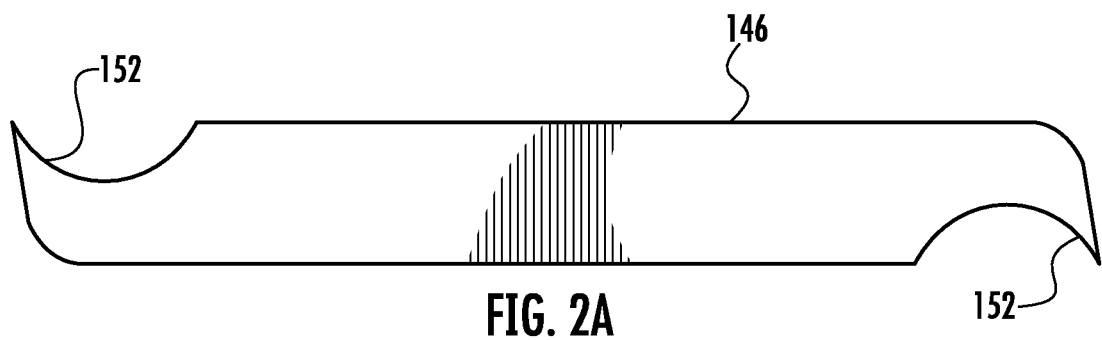
FIG. 2A is a cross-section view of an example blade.
Figure 2B:
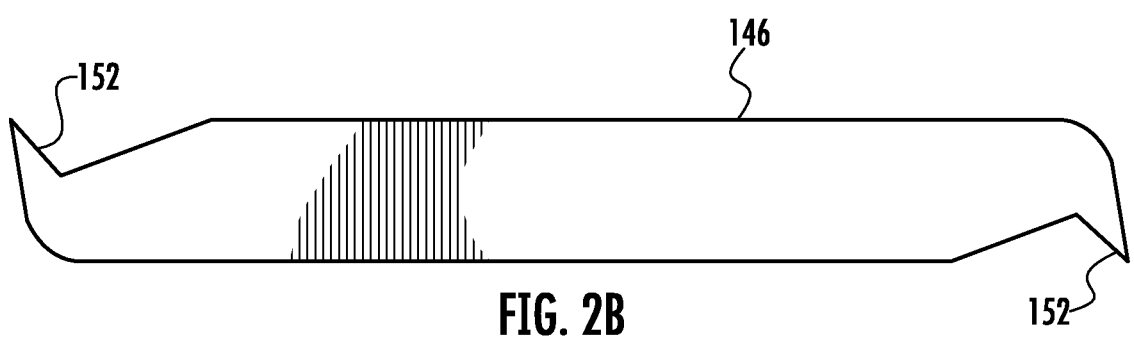
FIG. 2B is a cross-section view of an example blade.

The blade 146 can include a cutting surface 152 along the outer perimeter of the blade 146. The cutting surface 152 can be used for dislocating material from a target area within the intervertebral disc (e.g., nucleus and/or annulus material) and/or cancellous bone. The cutting surface 152 can define a continuous edge as provided in FIG. 1E. The cutting surface 152 can also define an interrupted edge. For example, as illustrated in FIGS. 1A-1D, 1F and 1G, the cutting surface 152 can include a plurality of grooves 154 to aid in removal of material as the cutting surface 152 moves along/impacts the target area. The grooves 154 can break/cut the material into smaller fragments thereby making them easier to transport away from the target area and out of the body of the patient. FIGS. 2A and 2B, provide an axial cross-section view of example blades 146. As illustrated in FIG. 2A, the cutting surface 152 can include a curved or rounded surface terminating at a sharpened point/edge. As illustrated in FIG. 2B, the cutting surface 152 can include an angled or chamfered surface terminating at a sharpened point/edge.

The blade 146 can also include a portion that is rotated around the longitudinal axis of the rotation mechanism 140. For example, as illustrated in FIGS. 1A-1D, 1F and 1G, the blade 146 can form a helical surface rotating around the longitudinal axis of the shaft 142. The angle of rotation/twist of the blade 146 can be determined to prevent a hammering effect on the interior disc/bone surface when the blade 146 is rotated. The hammering effect occurs when disc/bone material is impacted as a result of the height of the cavity created by the blade 146 varying during blade rotation. As a result, the angle of rotation/twist of the blade 146 can be determined such that the width/height defined by the rotated blade 146 generally constant.

Figure 3:
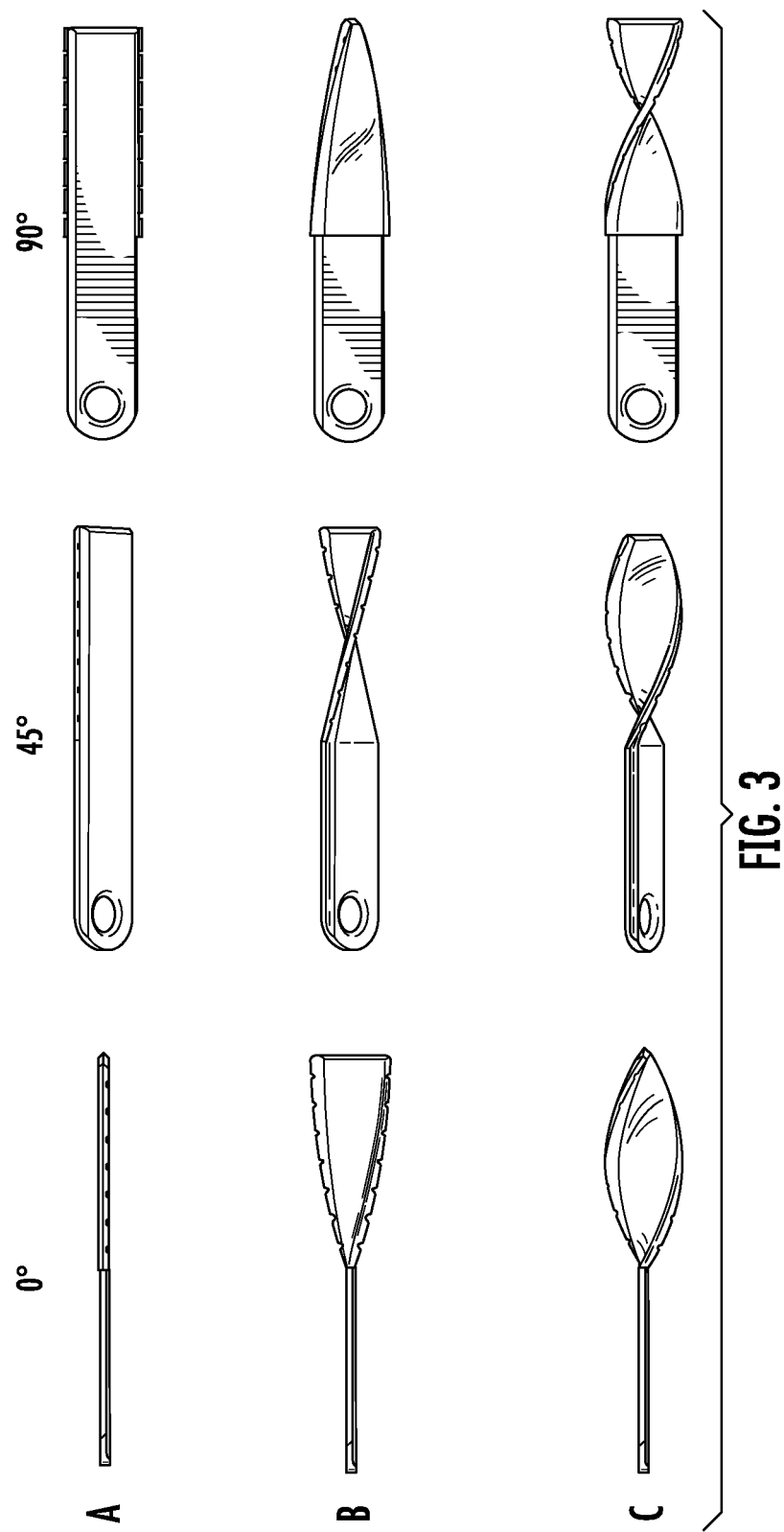
FIG. 3 is side views of example blades.

FIG. 3 provides an illustration of an example blade 146 rotated/twisted at various angles. Row A provides an example blade 146 with 0° of blade twist. From left to right in FIG. 3, the blade 146 is shown at various orientations. As the entire blade 146 is rotated between 0°, 45°, and 90°, the height defined by the blade 146, when viewed from the side, varies significantly. For example, Row A provides an example blade 146 having 0° of blade twist. At a 0° orientation, the blade 146 has a narrow height profile. The height profile increases drastically as the entire blade 146 is rotated through 45° and 90° orientation. It can be estimated that a blade 146 with 0° of blade twist can have a blade height that varies approximately 70%. Such a drastic variation in blade height can cause a hammering effect on opposing disk surfaces during rotation of the blade 146.

Row B provides an example blade 146 having approximately 90° if blade twist. From left to right in FIG. 3, as the entire blade 146 is rotated between 0°, 45°, and 90°, the height defined by the blade 146, when viewed from the side, can vary approximately 30%. This blade height variation can also cause a hammering effect on opposing disk surfaces during rotation of the blade 146.

Row C provides an example blade having approximately 180° of blade twist. From left to right in FIG. 3, as the entire blade 146 is rotated between 0°, 45°, and 90°, the change in height defined by the blade 146, when viewed from the side, is minimal (approximately null). As a result, the hammering effect is minimal.

Accordingly, in the present disclosure, an example blade 146 can have a blade twist less than about 90°. Another example blade 146 can have a blade twist of at least about 90°. Another example blade 146 can have a blade twist of at least about 180°. In a further example, the blade 146 can have a blade twist greater than about 180°.

Figure 4:
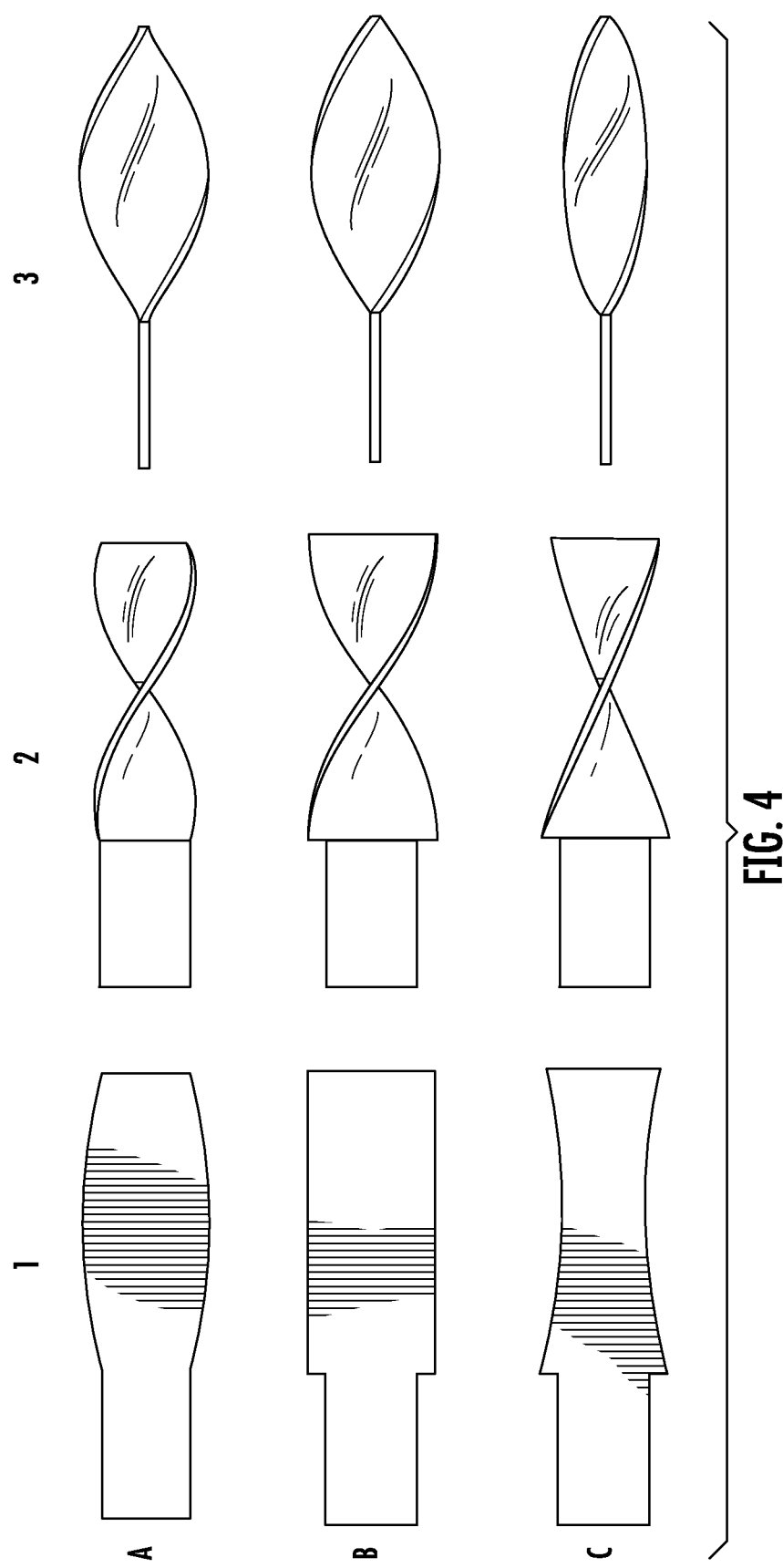
FIG. 4 is side views of example blade blanks.

The pre-twist/blank shape of the blade 146 can define any suitable regular or irregular shape. FIG. 4 provides an illustration of example blades 146 with various blank (pretwist) shapes (Column 1). For example, Row A provides an example blade 146 having a blank defining a rectangular shape with convex side edges that curve and extend radially. Row B provides an example blade 146 with a blank defining a rectangular shape with square corners and straight side edges. Row C provides an example blade 146 with a blank defining a rectangular shape with concave side edges that curve inward radially. The blank shape of the blade 146 can also be designed to maximize the contact of the cutting surface 152 with the target area. FIG. 4 illustrates the twisted blades 146 at an initial position (Column 2) and the twisted blades 146 rotated 90° (Column 3). As illustrated in Column 3, the amount of cutting surface 152 contacting the target area at a 90° rotation is greatest with the blade 146 design provided in Row C, a rectangular shape with concave side edges.

As illustrated in FIGS. 1A, 1B, 1D, 1E and 1G, the shaft 142 can also include projections 156 extending from the outer surface of the shaft 142 body. The projections 156 can form a helical (or spiral) surface extending around the shaft 142. The height of the projections 156 can be configured such that the rotation mechanism 140 is rotatable within the cannula 120. When rotated within the cannula 120, the shaft 142/projections 156 can act as a conveyor (or screw pump) for moving dislocated material from the target area and through the cannula bore 122. The projections 156 can include a plurality of flanks 158. When the flanks 158 come into contact with the dislocated material, rotation of the shaft 142/flanks 158 generates a force in the axial direction on the material.

Figure 8:
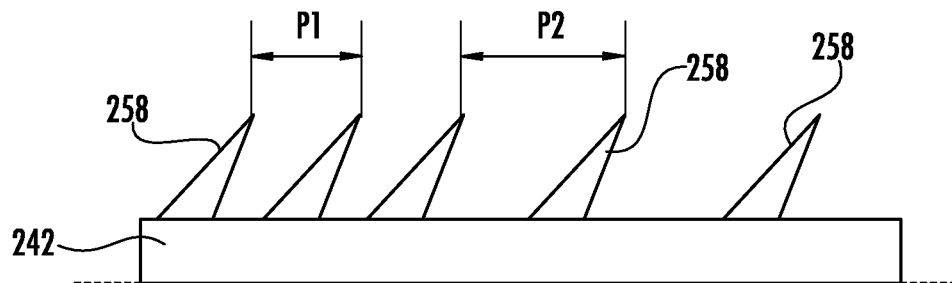
FIG. 8 is a partial side view of an example rotation mechanism.

As explained in more detail below with respect to FIG. 8, the pitch between various flanks 158 of the projections 156 can vary along the length of the shaft 142 to provide for different efficiency in removing dislocated material and/or help control the axial forces on the rotation mechanism 140. The pitch can be adjusted to define the rate of material removal as well as the particle size of the dislocated material capable of being transported through the cannula 120. In an example rotation mechanism 140 the pitch is uniform along the length of the shaft 142. In another example, the pitch varies between various flanks 158. Similarly, the length of the projections 156 along the longitudinal axis of the shaft 142 can be adjusted to provide for different efficiency in removing dislocated material and/or help control the axial forces on the rotation mechanism 140. In an example rotation mechanism 140, the projections 156 can extend from the shaft 142 along a portion of the shaft 142. In another example (not shown), the projections 156 can extend along the entire length of the shaft 142.

Figure 1H:
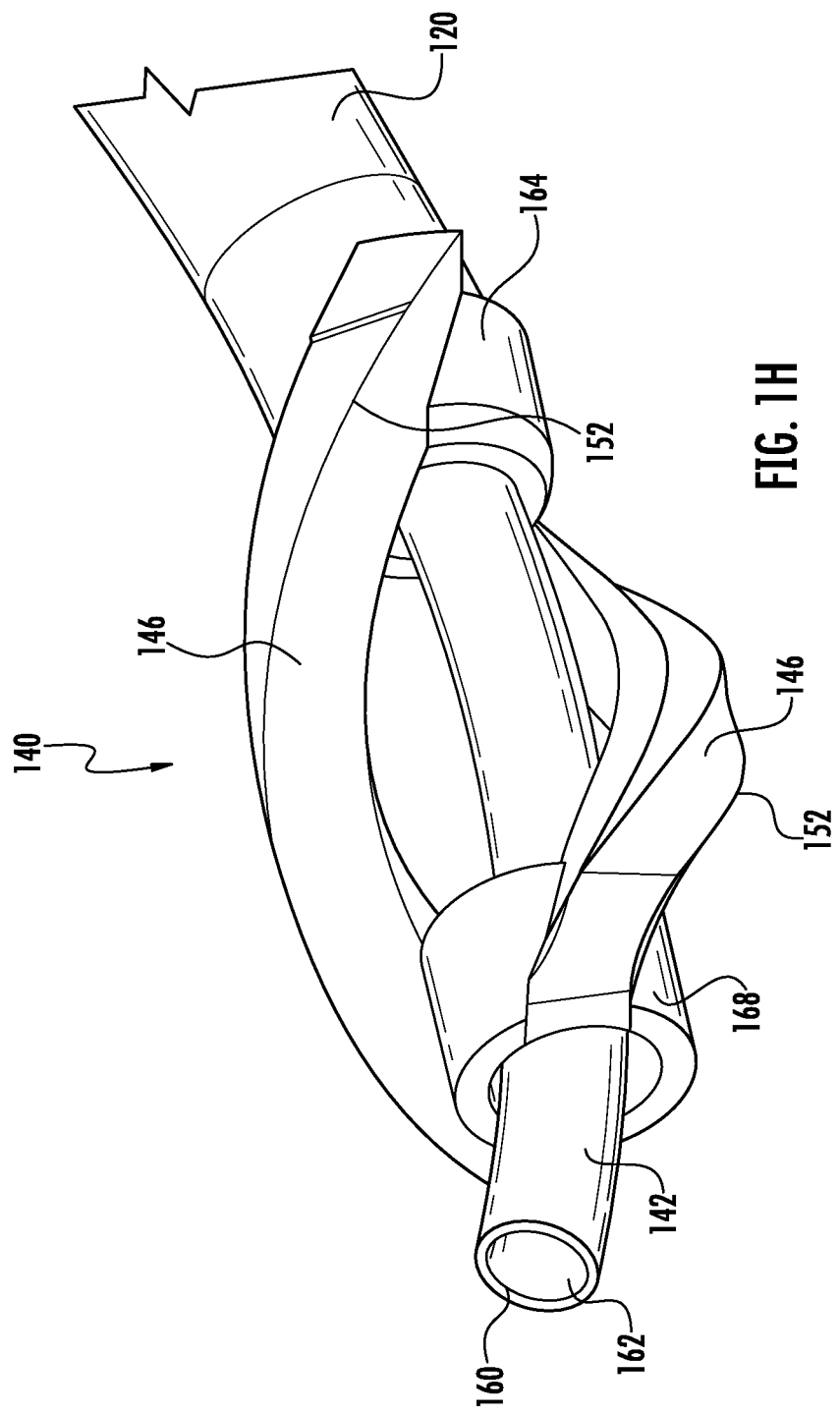
FIG. 1H is a partial perspective view of an example material removal instrument.

Another example rotation mechanism 140, illustrated in FIG. 1H, can include a plurality of blades 146 rotated around the longitudinal axis of the rotation mechanism 140 to form a plurality of helical surfaces. During operation, the blades 146 rotate around the longitudinal axis of the shaft 142. The blades 146 originate at a first terminal 164 and terminate at a second terminal 168. The first and second terminals 164, 168 can be operatively coupled to the elongated shaft 142. As outlined in more detail below, the rotation mechanism 140 and/or the cannula 120 can be formed from a flexible or rigid material to aid in direction and placement of the rotation mechanism at the target area.

The shaft 142 can include a central bore 160 and an opening 162 providing access to the central bore 160. The opening 162 can be located at the end of the shaft 142, as illustrated in FIGS. 1A-1H. In another example (not shown), the opening 162 can be located on a lateral surface of the shaft 142. The opening 162 can define any suitable shape including, for example, circular, elliptical, square, rectangular, or any other regular or irregular shape. An example rotation mechanism 140 may include multiple bore openings 162. For example, a bore opening 162 can be provided on each side of the blade 146. It is contemplated that the bore 160 can be used to provide irrigation to the target cutting area. The proximal end of the bore 160 can be operatively coupled to an irrigation source for providing irrigation at the bore opening 162. The irrigation can dissipate heat generated between the rotation mechanism 140 and the target area and/or heat generated between the rotation mechanism 140 and the cannula 120. The irrigation can also prevent dislocated material (e.g., soft tissue, bone, blood, or other interstitial fluid/materials) from adhering to the blade 146, projections 156, or inner surface of the cannula bore 122. The irrigation also aids in the flow of the dislocated material from the target area through the cannula 120. It is further contemplated that the bore 160 can be sized and configured to receive a guide wire to direct placement of the rotation mechanism 140. In another example (not shown), the shaft 142 can include a solid structure, without including a bore 160.

As illustrated in FIGS. 1A-1D and 1F-1H, the rotation mechanism 140 can be disposed within a cannula 120. The cannula 120 is sized and configured to permit rotation of the rotation mechanism 140. The cannula 120 can also function as a torque transmission element with respect to dislocated material passing through the cannula bore 122 and/or the rotation mechanism 140. In an example rotation mechanism 140, rotational movement of the cannula 120 can be fixed. In another example, the cannula 120 can rotate in the same or opposite direction of the rotation mechanism 140. The cannula 120 can define an elongated cylindrical structure. The cannula 120 can be constructed from a flexible material (e.g., polymers, Nitinol) or a rigid material. An example cannula 120 constructed from a stiff and/or rigid material can include structural modification (e.g., geometric cutouts or shapes) that provide an overall flexible behavior regarding cross forces.

An example cannula 120 can have an outer diameter ranging from about 3 mm to about 6 mm. In another example, the cannula 120 can have an outer diameter ranging from about 5 mm to about 6 mm. In a further example, the cannula 120 can have an outer diameter of about 5.5 mm. The cannula 120 can include a central bore 122 sized and configured to accommodate the rotation mechanism 140. The inner diameter of the central bore 122 can range from about 2 mm to about 5 mm. The cannula 120 can also include an opening 124 providing access to the central bore 122. The opening 124 can be located on the rotation mechanism 140 such that at least a portion of the blade 146 is provided access to the target area when the material removal instrument 100 is located within the patient. The opening 124 can be located at the end of the cannula 120, as illustrated in FIGS. 1A-D and 1F-1H. In this example, the rotation mechanism 140, including at least a portion of the blade 146, can extend from the cannula opening 124. In another example (not shown), the opening 124 can be located on a lateral surface of the cannula 120. In this example, the cannula opening 124 can be sized and located such that at least a portion of the rotation mechanism 140, including at least a portion of the blade 146, extends from the cannula opening 124. The opening 124 can define any suitable shape including, for example, circular, elliptical, square, rectangular, or any other regular or irregular shape.

Figure 5:
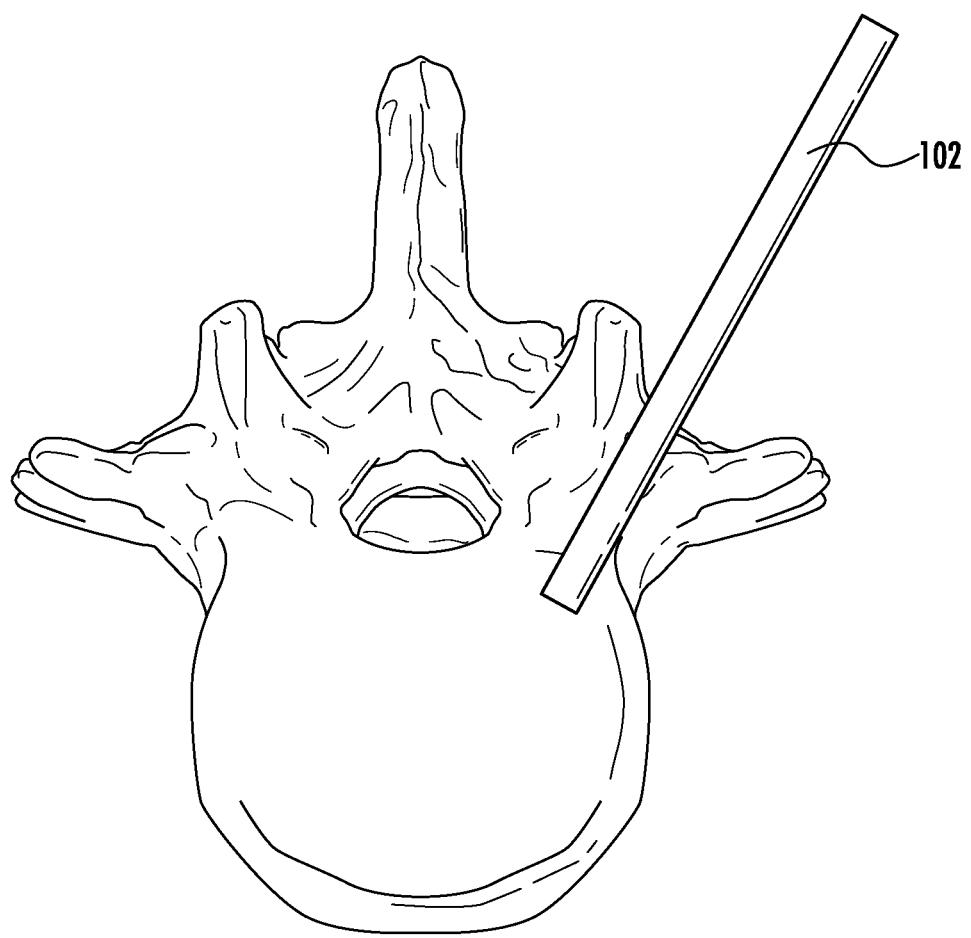
FIG. 5 is a superior view of an example disc and inferior vertebral body.

In use, the material removal instrument 100 can remove bony material and/or disc material between adjacent and/or within vertebrae. When used for removal of disc material (e.g., discectomy), disc access can be gained via a posterior and/or posterolateral percutaneous, extrapedicular approach. If a guide wire is used, it can be inserted into the disc. As provided in FIG. 5, an introducer cannula 102 can be slid over the guide wire and introduced into the disc space. An example introducer cannula 102 can have an outer diameter of about 3 mm to about 7 mm. The cannula 120 and rotation mechanism 140 can then be provided into the disc space via the introducer cannula 102. The material removal instrument 100 (cannula 120 and rotation mechanism 140) can be located such that the cannula opening 124 is proximate the target area within the disc. Once positioned at the target area, the rotation mechanism 140 can be rotated within the cannula 120 causing the blade 146 to contact and dislocate disc material at the target area and thereby create a cavity, e.g., within the disc space. In an example material removal instrument 100, the proximal end 150 of the rotation mechanism 140 can be operatively coupled to a source of rotation energy.

The dislocated material can be drawn into the cannula opening 124 and through the cannula bore 122. As outlined above, rotation of the rotation mechanism 140 can create pumping action that urges the dislocated tissue into the cannula opening 124 and through the cannula bore 122 without the use of supplemental aspiration/suction. In another example, the proximal end of the cannula bore 122 can be operatively coupled to a suction device to aid in removal of the dislocated material from the target area and/or the cannula bore 122.

The material removal instrument 100 can be withdrawn from the cavity and a treatment element can be provided to the disc space. The treatment element can include, for example, a filler material and/or an inflatable body, such as those used for kyphoplasty. The filler material can include, for example, bone cement, bone chips, demineralized bone, and/or an implant.

Figure 6A:
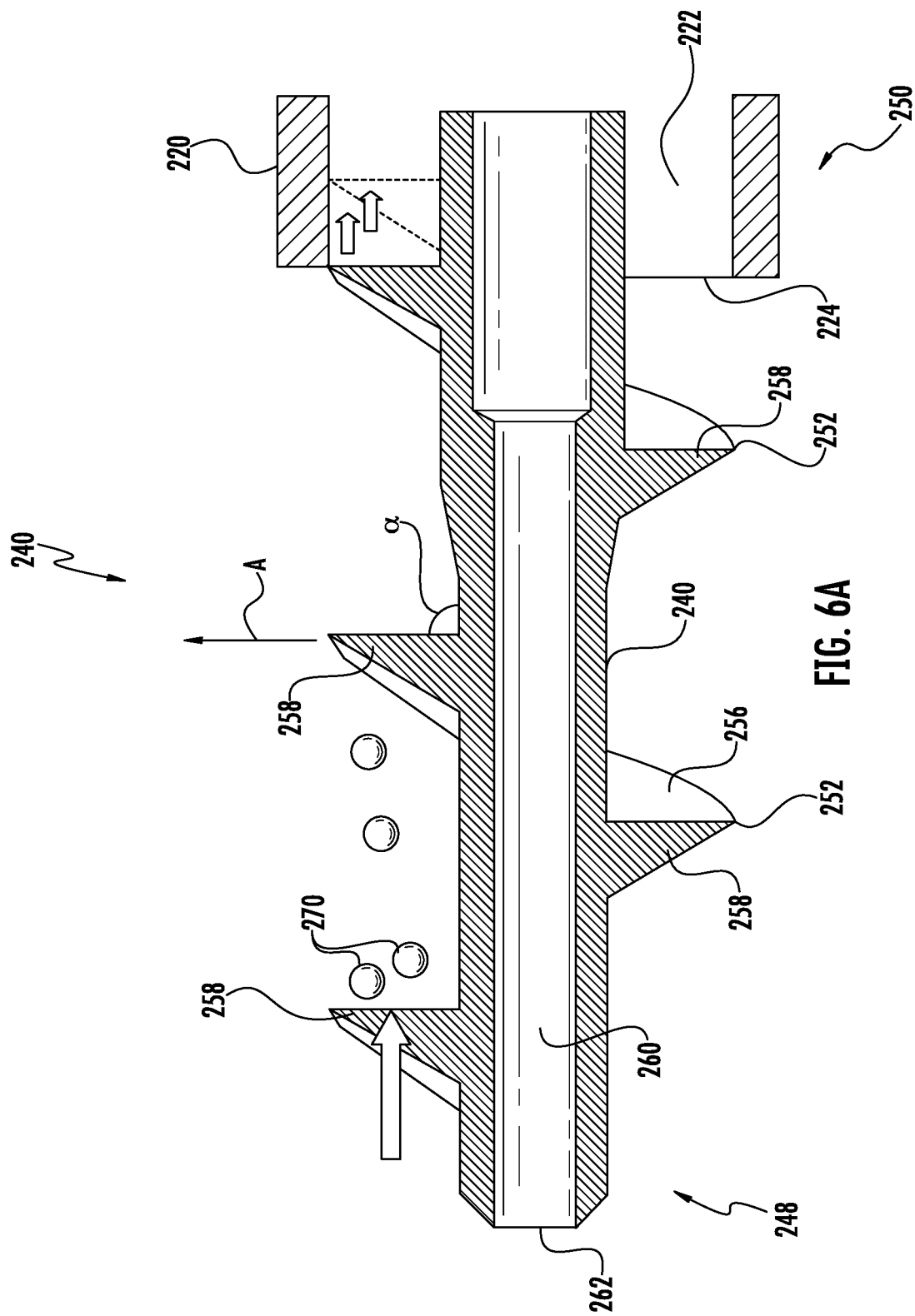
FIG. 6A is a side cross-section view of an example rotation mechanism.
Figure 6B:
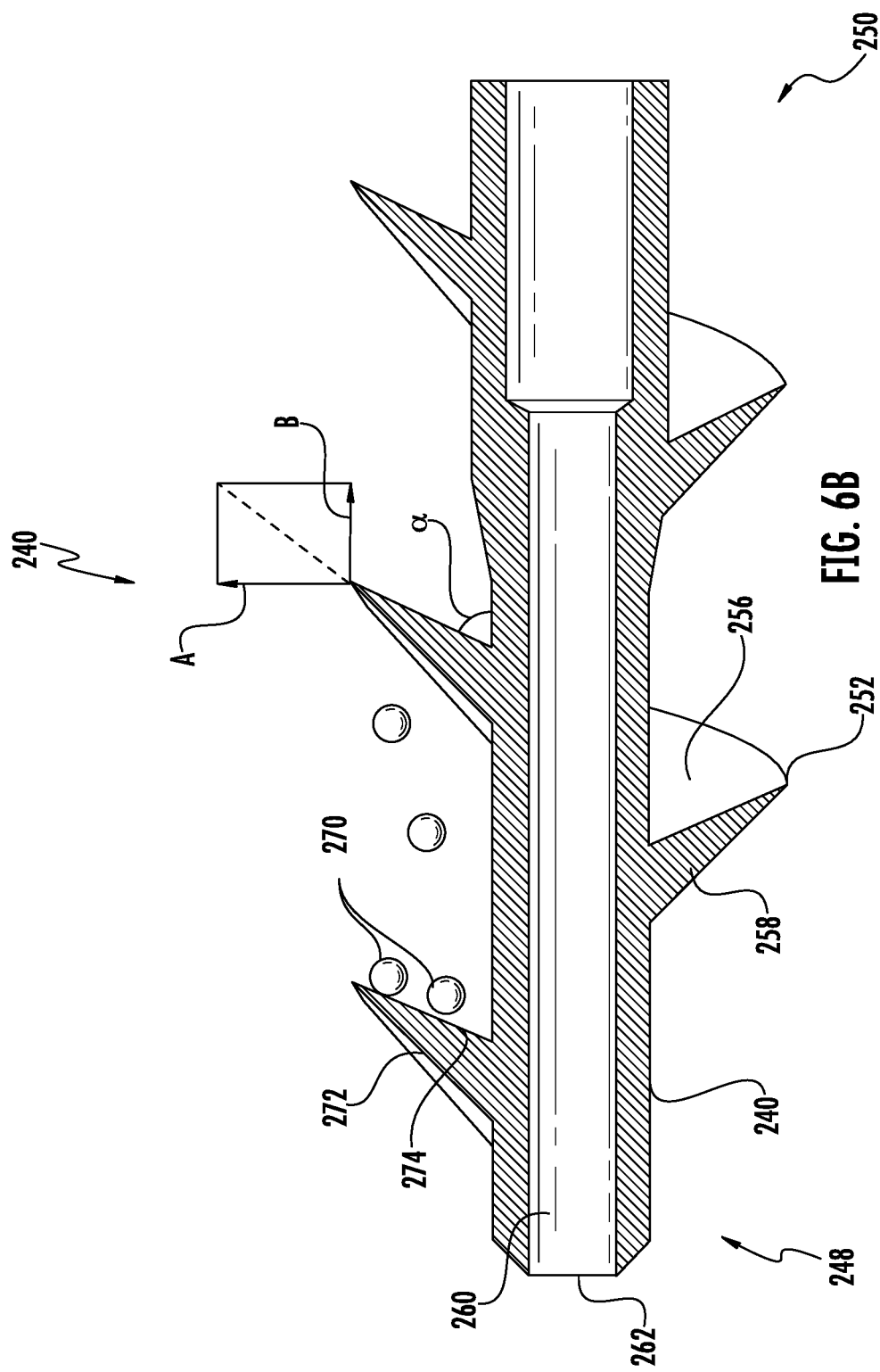
FIG. 6B is a side cross-section view of an example rotation mechanism.
Figure 6C:
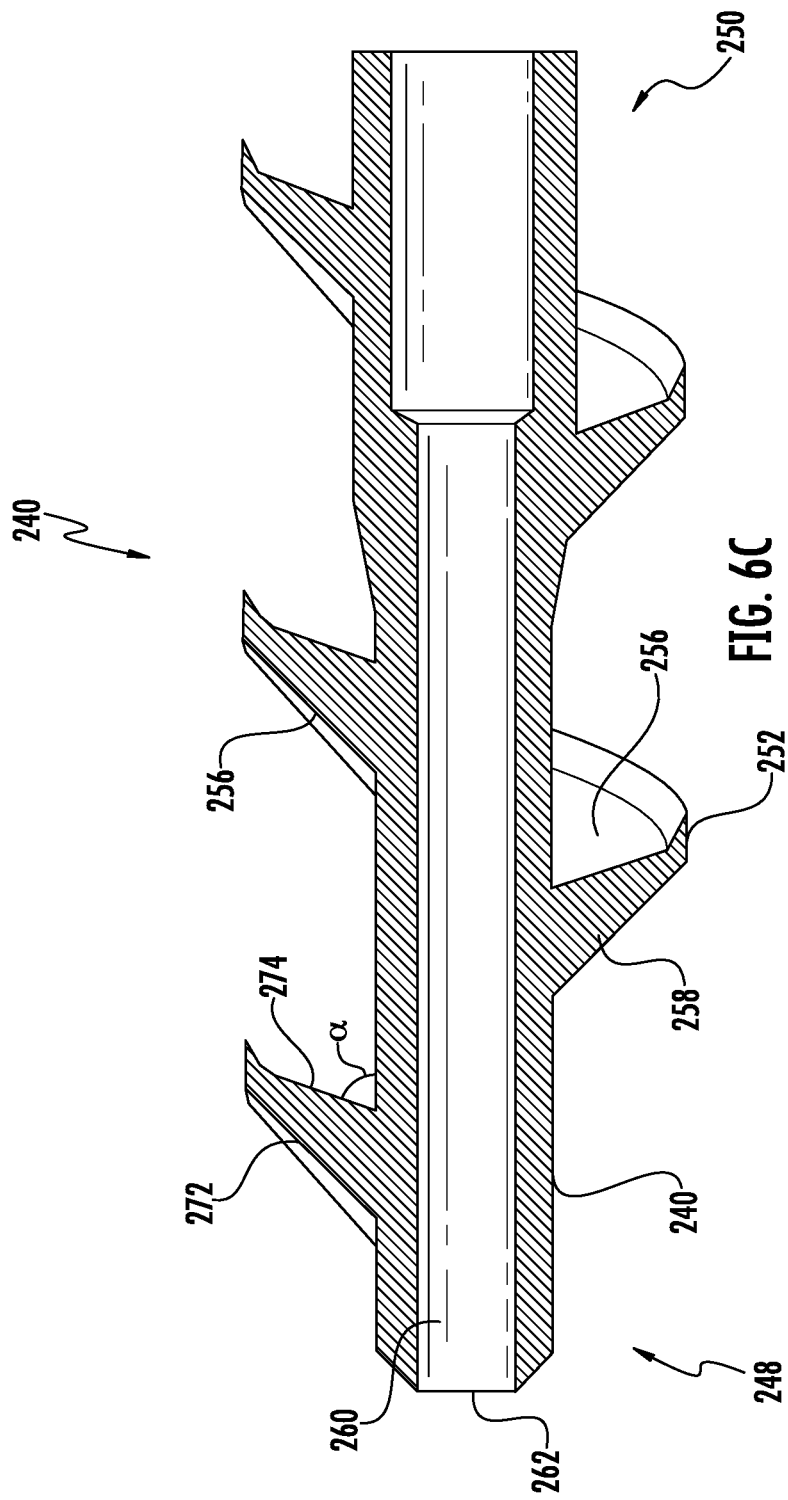
FIG. 6C is a side cross-section view of an example rotation mechanism.

FIGS. 6A-6C provide side cross-section views of another example material removal instruments 200. The example material removal instrument 200 can include a cannula 220 and a rotation mechanism 240. The rotation mechanism 240 can include a shaft 242. The shaft 242 can define an elongated cylindrical structure. In another example (not shown), the shaft 242 can define an elongated structure with a cross-section having any suitable shape including, for example, elliptical, square, rectangular, or any other regular or irregular shape. As outlined above with respect to shaft 142, the shaft 242 can be constructed from a flexible material (e.g., polymers, Nitinol) or a rigid material. An example shaft 242 constructed from a stiff and/or rigid material can include structural modification (e.g., geometric cutouts or shapes) that provide an overall flexible behavior regarding cross forces. The flexibility of the shaft 242 can also be achieved by a linkage (not shown) between the cutting surface 252 and the flanks 258.

The shaft 242 can include a central bore 260 and an opening 262 providing access to the central bore 260. The opening 262 can be located at the end of the shaft 242, as illustrated in FIGS. 6A-6C. In another example (not shown), the opening 262 can be located on a lateral surface of the shaft 242. The opening 262 can define any suitable shape including, for example, circular, elliptical, square, rectangular, or any other regular or irregular shape. An example rotation mechanism 240 may include multiple bore openings 262. It is contemplated that the bore 260 can be used to provide irrigation to the target cutting area. The proximal end of the bore 260 can be operatively coupled to an irrigation source for providing irrigation at the bore opening 262. The irrigation can dissipate heat generated between the rotation mechanism 240 and the target area and/or heat generated between the rotation mechanism 240 and the cannula 220. The irrigation can also prevent dislocated material (e.g., soft tissue, bone, blood, or other interstitial fluid/materials) from adhering to the threads 256 or inner surface of the cannula bore 222. The irrigation also aids in the flow of the dislocated material from the target area through the cannula 220. It is further contemplated that the bore 260 can be sized and configured to receive a guide wire to direct placement of the rotation mechanism 240. In another example (not shown), the shaft 242 can include a solid structure, without including a bore 260.

The shaft 242 can include a thread 256 extending from the outer surface of the shaft 242 body. The thread 256 can form a helical (or spiral) surface extending around the shaft 242. The thread 256 can extend from the shaft 242 along the entire length of the shaft 242. In another example, the thread 256 can extend along only a portion of the length of the shaft 242. The thread 256 can include a cutting surface 252 along the outer perimeter of the thread 256 for dislocating material from the target area within the intervertebral disc (e.g., nucleus and/or annulus material) and/or cancellous bone. As illustrated in FIG. 6C, the cutting surface 252 can include an edge extending towards the proximal end 250 of the shaft 242. The example cutting surface 252 can be used to dislocate material from the target area and help to retain the dislocated material behind the flanks 258 for during rotation of the shaft 242.

Rotation of the shaft 242 can cause the cutting surface 252 to contact and dislocate material in the target area. Similarly, rotation of the shaft 242 can cause the thread 256 to act as a conveyor for moving the dislocated material 270 from the target area towards the proximal end 250 of the shaft 242 (similar to the projections 156 included in the rotation mechanism 140).

The thread 256 can include a plurality of flanks 258. In another example (not shown), the thread 256 can include a single flank 258. Each flank 258 can include a leading side 272 and a trailing side 274. Each flank 258 can define a flank angle ($\alpha$). For the purpose of this application, the flank angle ($\alpha$) will be defined with respect to the trailing side 274 of the flank 258 and a reference plane parallel with the longitudinal axis of the shaft 242. In the example rotation mechanism 240 illustrated in FIG. 6A, the flank angle ($\alpha$) defined by the flank 258 is approximately 90°. A thread 256 having a 90° flank angle ($\alpha$) provides a single cutting direction perpendicular to the longitudinal axis of the shaft 242, a radial component (as represented by Arrow A). To provide a cutting direction in the parallel to the longitudinal axis of the shaft 242 (an axial component), the rotation mechanism 240 can include a cannula 220 that functions as a shearing sleeve. As the dislocated material 270 is transported towards the proximal end 250 of the shaft 242 and the cannula 220, the interface between the flank 258 and the cannula 220 can detach the material from the target location and/or rupture the material into smaller pieces. Because the interface between the flank 258 and the cannula 220 provides an additional dislocation point for the material, it is not necessary that the cutting surface 252 of the thread 256 be as sharp as when the cannula 220 is not used as a shearing sleeve.

In another example, illustrated in FIG. 6B, the flank angle ($\alpha$) can be an angle less than 90°. For example, the flank angle ($\alpha$) range between about 30° and less than about 90°. In another example, the flank angle ($\alpha$) can range between about 45° and less than about 90°. In a further example, the flank angle ($\alpha$) can be about 70°. With a flank angle ($\alpha$) less than 90° can result in better retention and transport of dislocated material 270 via rotation of the thread 256. In another example (not shown), an example rotation mechanism 240 with a flank angle ($\alpha$) less than 90° can include a cannula 220 functioning as a shearing sleeve, as described above with respect to FIG. 6A.

Figure 7A:
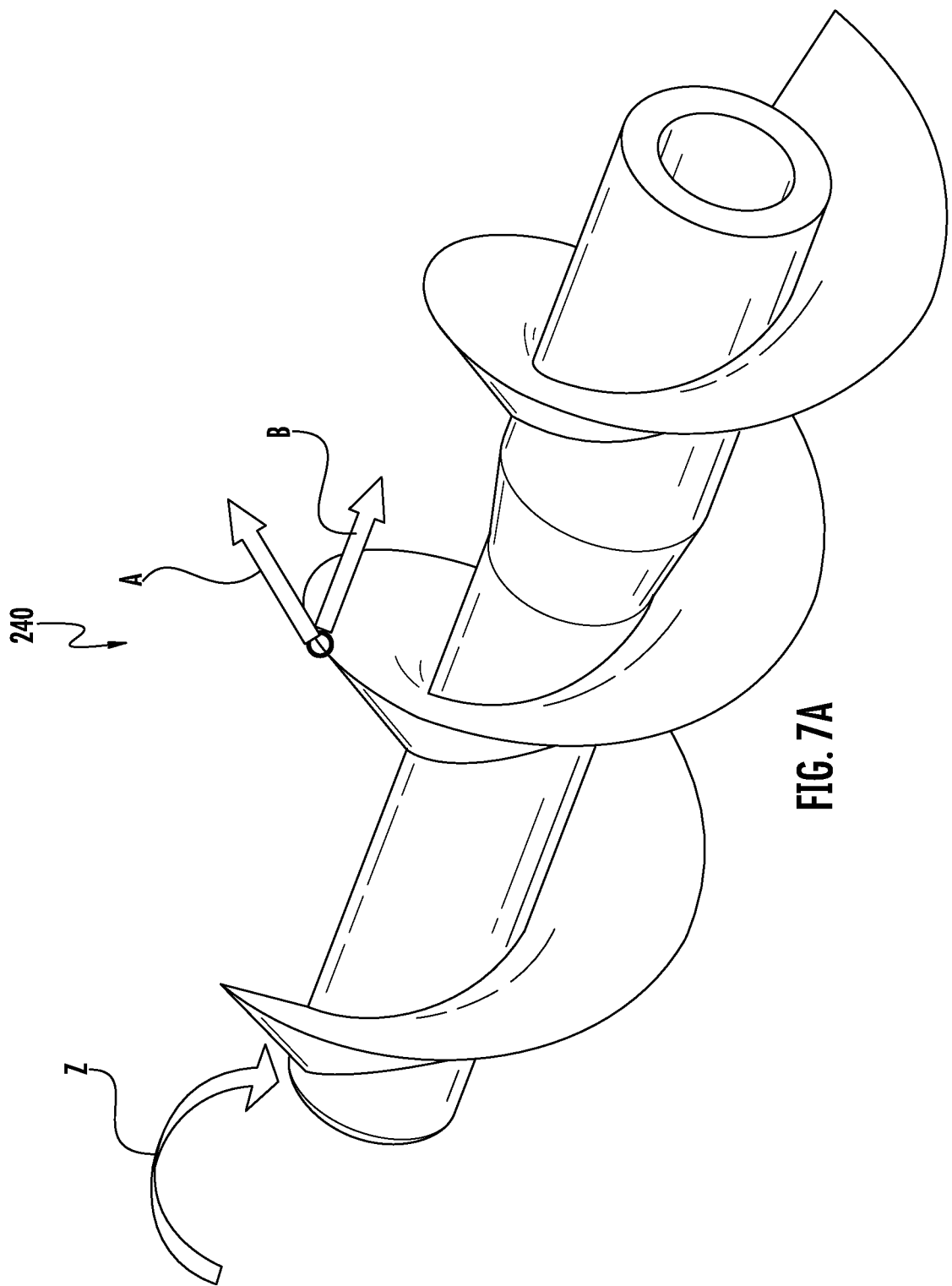
FIG. 7A is a perspective view of an example rotation mechanism.
Figure 7B:
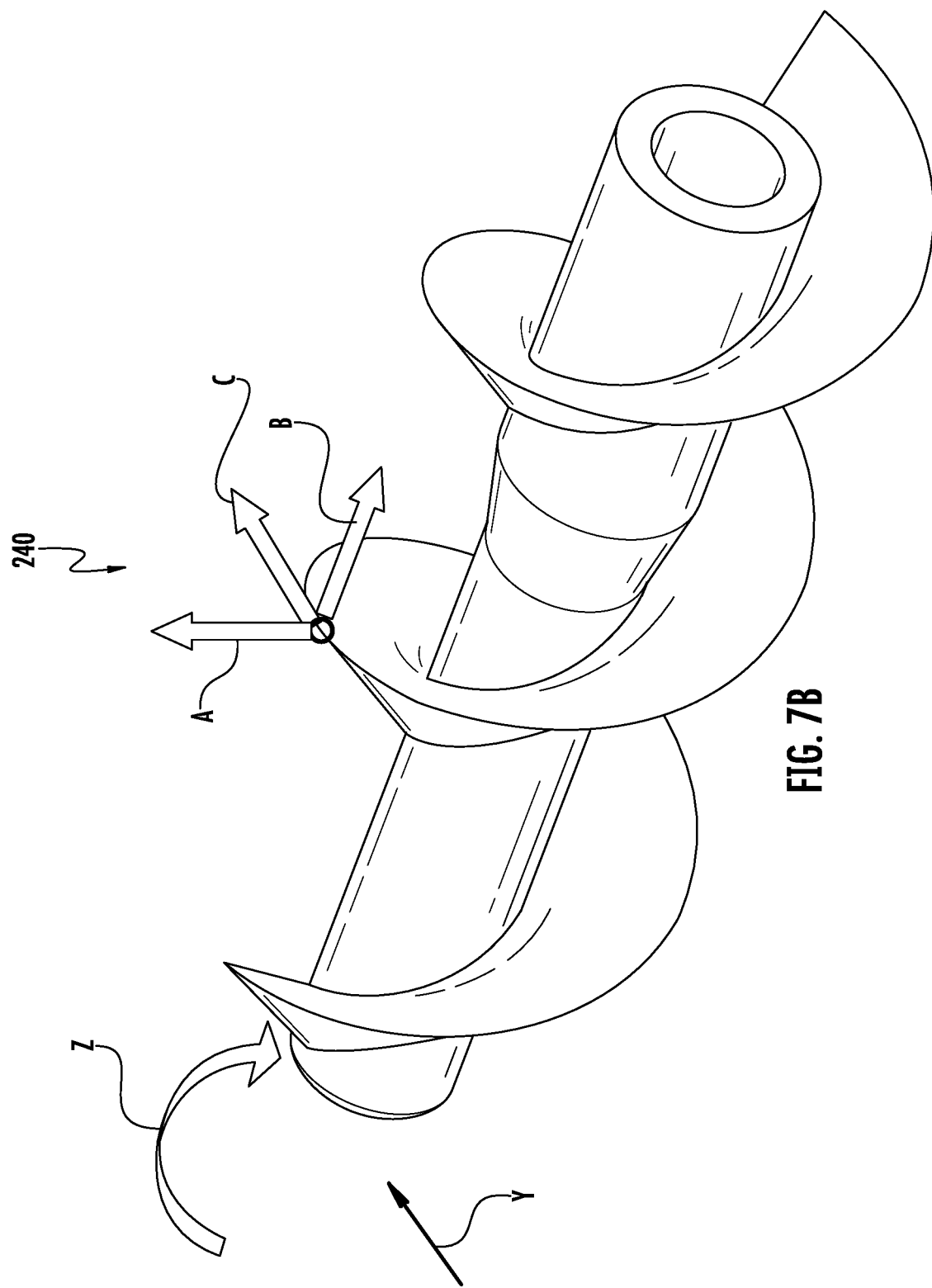
FIG. 7B is a perspective view of an example rotation mechanism.

During rotation, a thread 256 having a flank angle ($\alpha$) less than 90° provides a cutting directions perpendicular to the longitudinal axis of the shaft 242, a radial cutting component (represented by Arrow A), and a cutting direction parallel to the longitudinal axis of the shaft 242, an axial cutting component (as represented by Arrow B). FIG. 7A provides a perspective view of the example rotation mechanism 240 illustrating the radial (Arrow A) and axial (Arrow B) cutting components when the shaft # is rotated (Arrow Z). A third cutting direction can be provided by moving the shaft 242 in the lateral (side-to-side) or vertical (up-an-down) direction. As illustrated in FIG. 7B, rotation of the rotation mechanism 240 (Arrow Z), provides a radial cutting component (Arrow A) and an axial cutting component (Arrow B). Movement of the distal end rotation mechanism # in the vertical direction (Arrow Y) provides a lateral cutting component (Arrow C).

As outlined above with respect to the rotation mechanism 240 works to remove dislocated material from the target by rotation of the threads 256 (similar to rotations mechanism 140 and projections 156). As the rotation mechanism 240/threads 256 urge the dislocated material towards the proximal end 250 of the shaft 242, forces in the opposite direction direct ("pull") the rotation mechanism 240 in the direction towards the distal end 248. That is, consistent with Newton's third law of motion, when the rotation mechanism 240/threads 256 exert a force (F1) on the material in the target area, the material simultaneously exerts a force (F2) on the rotation mechanism 240. These forces are generally equal in magnitude and opposite in direction. This force on the rotation mechanism 240 can causes the shaft 242 to "crawl" forward in the target area making control of the rotation mechanism 240 challenging.

Varying the pitch between various flanks 258 of the thread 256 along the length of the shaft 242 can help control the resultant axial forces on the rotation mechanism 240 (including the forward force) and can control the efficiency in removing dislocated material. That is, the pitch width can be adjusted to adjust the force in the axial direction on the material (e.g., the thrust effect on the dislocated material particles) and thereby dissipate the forward force on the rotation mechanism 240. The pitch can also be adjusted to define the rate of material removal as well as the particle size of the dislocated material capable of being transported from the target area. As provided in FIG. 8, the pitch between various flanks 258 can vary. For example, the pitch (P1) between a first set of flanks can be less than the pitch (P2) between a second set of flanks. In another example rotation mechanism 240, illustrated for example in FIGS. 6A-6C, the pitch between various flanks 258 is uniform along the length of the shaft 242.

Figure 9:
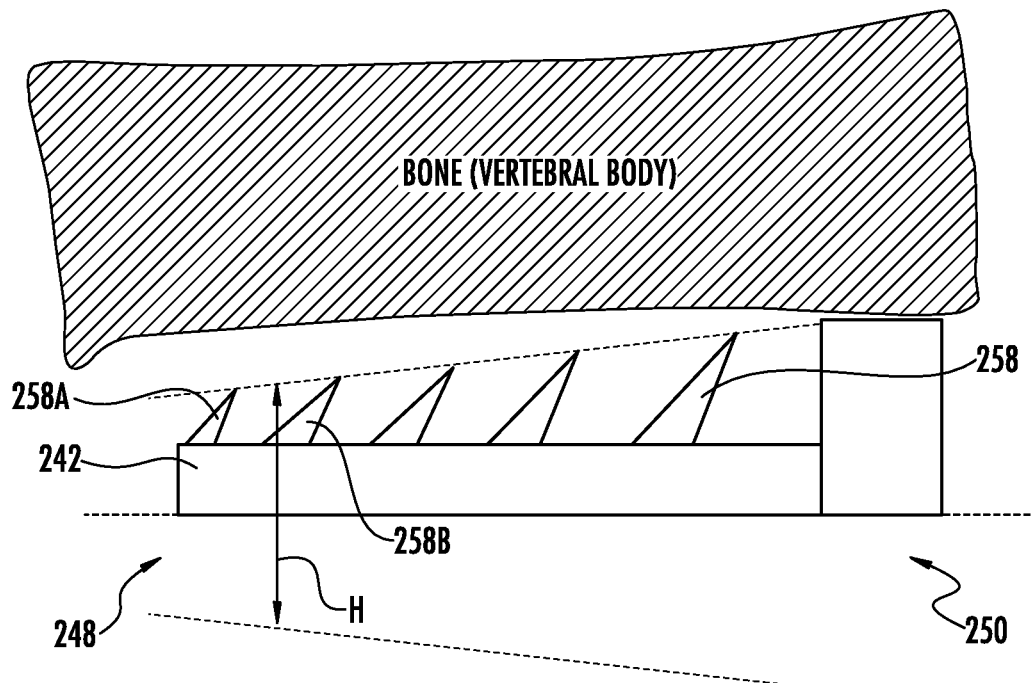
FIG. 9 is a partial side view of an example rotation mechanism.

Varying the height of the flanks 258 along the length of the shaft 242 can also be adjusted to control the resultant axial forces on the rotation mechanism 240 and provide for different efficiency in removing dislocated material. In general, the height of the flanks 258 is configured such that the rotation mechanism 240 can pass through and rotate within the cannula 220. FIG. 9 provides a partial side view of an example rotation mechanism 240 located within the disc space between the adjacent vertebral bodies. As illustrated in FIG. 9, the height of various flanks 258 can vary along the length of the shaft 242. For example, the height of the first flank 258A can be less than the height of the second flank 258B, and the overall flank height (H) progressively increases from the distal end 248 towards the proximal end 250. The flank height can be configured such that the flanks 258 located towards the proximal end 250 of the shaft 242 are proximate the surface of the superior and/or inferior vertebral body while the flanks 258 at the distal end 248 of the shaft 242 can impact and dislocate material without coming into contact with bony components. In another example rotation mechanism illustrated in FIGS. 6A-6C, the height of the flanks 258 can remain constant along the length of the shaft 242.

Varying the length of the thread 256 along the longitudinal axis of the shaft 242 can also be adjusted to control the resultant axial forces on the rotation mechanism 240 and provide for different efficiency in removing dislocated material. In the example rotation mechanism 240 illustrated in FIG. 11B, the thread 256 can extend from the shaft 242 along a portion of the shaft 242. In another example illustrated in FIGS. 6A and 6B, the projections 156 can extend along the entire length of the shaft 142.

Figure 10:
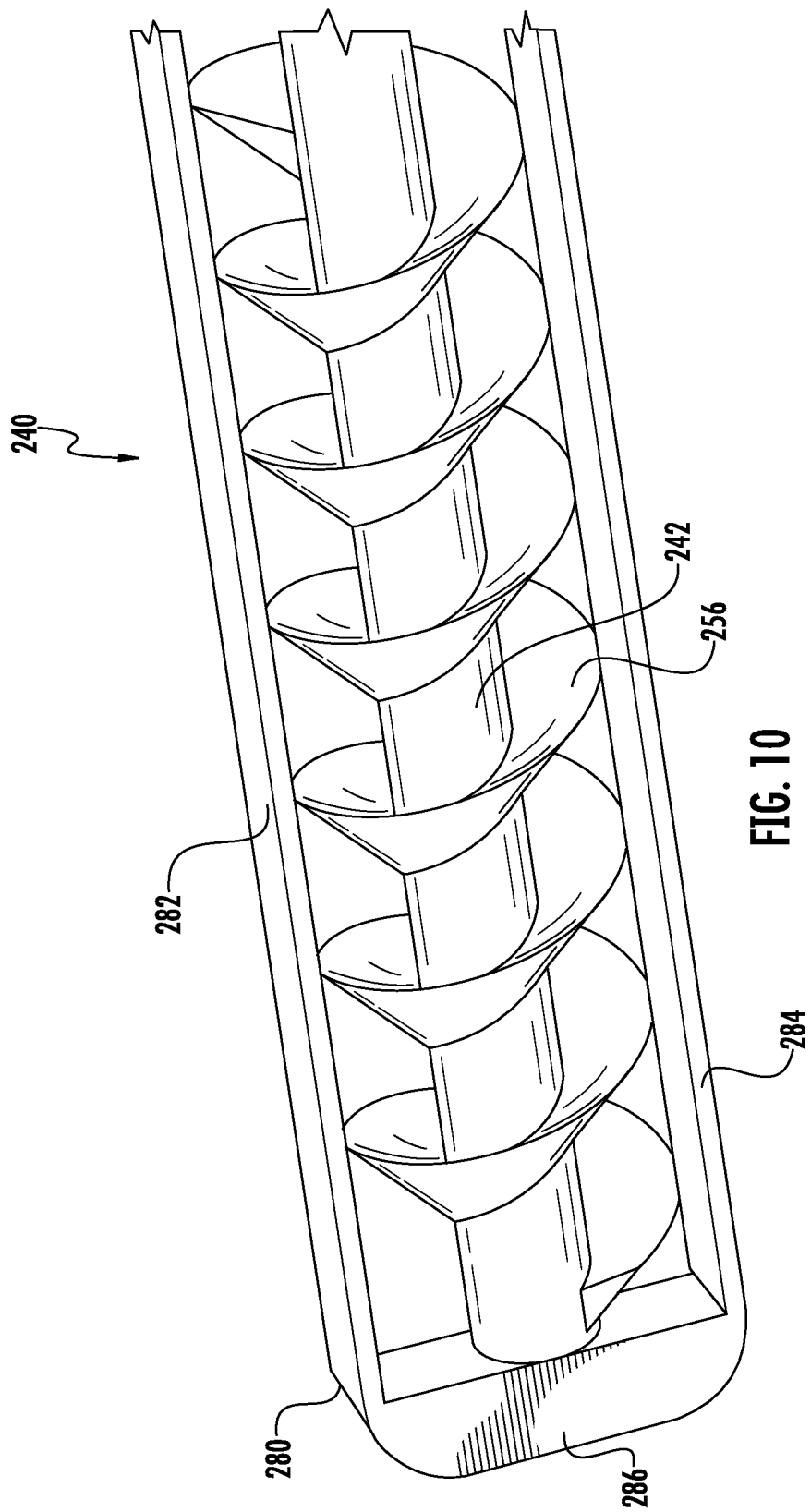
FIG. 10 is a partial perspective view of an example rotation mechanism.

The axial forces on the rotation mechanism 240 can also be controlled by the use of a housing surrounding a portion of the rotation mechanism 240. As illustrated in FIG. 10, the housing can include a sleeve 280 that partially covers the shaft 242 and the threads 256. The shaft 242 can rotate within the sleeve 280. The sleeve 280 can include a first arm 282 and a second arm 284 and a distal end 286. The shaft 242 can matingly engage the distal end 286. In another example, the shaft 242 is independent of the distal end 286. The open space between the first arm 282 and the second arm 284 can provide the threads 256 access to material at the target area. In the example rotation mechanism 240, when inserted into an intervetebral space, the first arm 282 and the second arm 284 can protect material adjacent to and/or associated the superior and inferior vertebra, while providing cutting windows in the posterior and anterior direction.

The rotation mechanism 240 can be disposed within a cannula 220. The cannula 220 can be similar in form and function to cannula 120. The cannula 220 is sized and configured to permit rotation of the rotation mechanism 240. The cannula 220 can be constructed from a flexible material (e.g., polymers, Nitinol) or rigid material. An example cannula 220 constructed from a stiff and/or rigid material can include structural modification (e.g., geometric cutouts or shapes) that provide an overall flexible behavior regarding cross forces. As outlined above, the cannula 220 can also function as a torque transmission element with respect to dislocated material passing through the cannula bore 222 and/or the rotation mechanism 240.

The cannula 220 can define an elongated cylindrical structure having an outer diameter ranging from about 3 mm to about 15 mm. In another example, the cannula 220 can have an outer diameter ranging from about 5 mm to about 6 mm. In a further example, the cannula 220 can have an outer diameter of about 5.5 mm. The cannula 220 can include a central bore 222 sized and configured to accommodate rotation of the rotation mechanism 240. The inner diameter of the bore 222 can range from about 1 mm to about 5 mm. The cannula 220 can also include an opening 224 providing access to the central bore #. The opening 222 can be located with respect to the rotation mechanism 240 such that at least a portion of the threads 256 is provided access to the target area when the material removal instrument 200 is located within the patient.

Figure 11A:
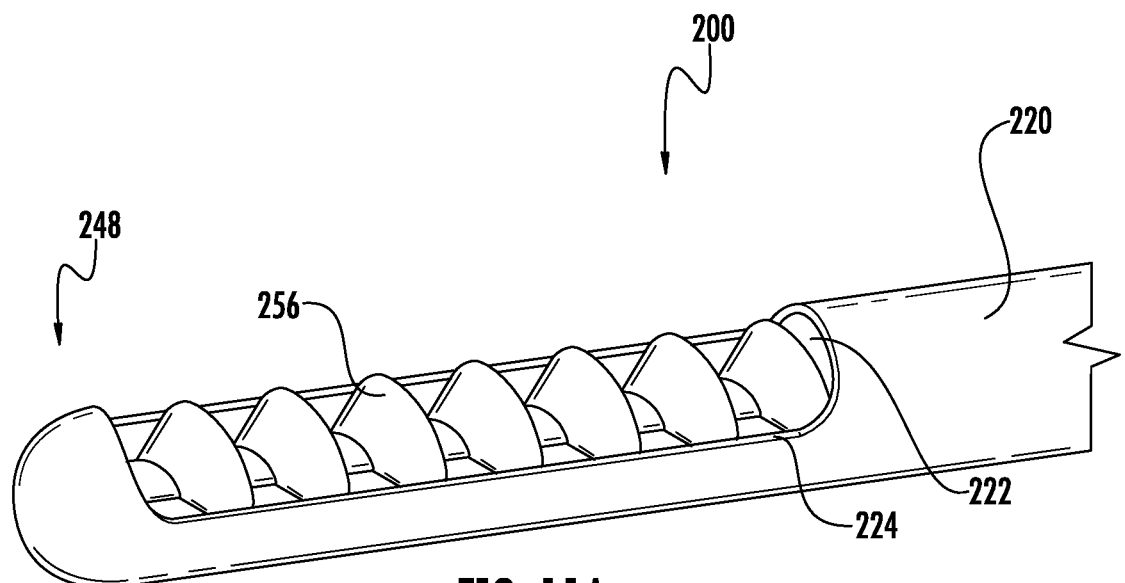
FIG. 11A is a partial perspective view of an example material removal instrument.
Figure 11B:
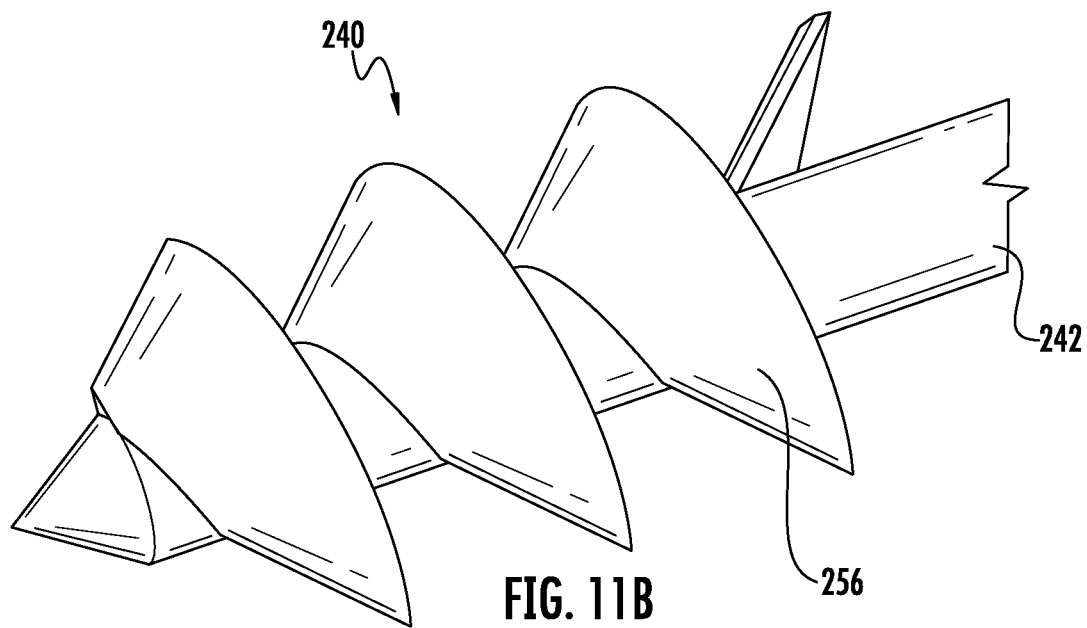
FIG. 11B is a partial perspective view of an example rotation mechanism.

As illustrated in FIGS. 11A and 11B, the opening 222 can be located on a lateral surface of the cannula 220. In this example, the cannula opening 222 can be sized and located such that at least a portion of the rotation mechanism 240, including at least a portion of the threads 256, extends from the cannula opening 224, thereby limiting cutting in the direction of the opening 224. The opening 224 can define any suitable shape including, for example, circular, elliptical, square, rectangular, or any other regular or irregular shape. The cannula 220 can include a single opening 224 or a plurality of openings 224 (not shown). In another example (not shown), the opening 224 can be located at the end of the cannula 220 and the rotation mechanism 240, including at least a portion of the threads 256 can extend from the cannula opening 224.

The cannula 220 can also be used to control the axial forces on the rotation mechanism 240. As illustrated in FIGS. 11A and 11B, the cannula 220 partially covers the shaft 242 and the threads 256. As provided in FIG. 11A, the opening 224 can be located on a lateral surface of the cannula and can define an elongated opening extending in both the longitudinal and radial surfaces of the cannula 220. By providing an opening 224, only those portions of the thread 256 proximate the opening 224 come in contact with material at the target area with a corresponding other portion of the thread 256 are not in contact with the material, thereby the axial forces resulting from rotation of the shaft 242 and contact with material at the target area are reduced. The cannula 220 can cover the distal end 248 of the rotation mechanism 240. By covering the distal end of the rotation mechanism 240, the cannula 220 helps prevent axial force on the rotation mechanism 240 from driving the rotation mechanism 240 forward. Covering the distal end 248 of the rotation mechanism 240 also helps prevent unintentionally removing excess material and/or damaging unintended tissue.

In use, the material removal instrument 200 can remove bony material and/or disc material between adjacent vertebrae. The cannula 220 and rotation mechanism 240 can be provided into the disc/bone space. The material removal instrument 200 (cannula 220 and rotation mechanism 240) can be located such that the cannula opening 224 is proximate the target area within the disc. Once positioned at the target location and the rotation mechanism 240 operatively coupled to a source of rotation energy, the rotation mechanism 240 can be rotated within the cannula 220 causing the threads 256 to contact and dislocate disc material at the target location and create a cavity within the disc space.

The dislocated material can be drawn into the cannula opening 224 and through the cannula bore 222. As outlined above, rotation of the rotation mechanism 240 and threads 256 can act as a conveyor (or screw pump) for moving dislocated material from the target area and through the cannula bore # without the use of supplemental aspiration/suction. In another example, the proximal end of the cannula bore 222 can be operatively coupled to a suction device to aid in removal of the dislocated material from the target area and/or the cannula bore 222.

FIGS. 12A-12D provide partial views of another example material removal instrument 300. The example material removal instrument 300 can include a cannula 320 and a rotation mechanism 340. The rotation mechanism 340 can include a shaft 342. The shaft 342 can define an elongated cylindrical structure. In another example (not shown), the shaft 342 can define an elongated structure with a cross-section having any suitable shape including, for example, elliptical, square, rectangular, or any other regular or irregular shape. As provided in FIG. 12A, the shaft 342 can define a first portion 370 having a first diameter and a second portion 372 having a second diameter. In another example rotation mechanism 340, the diameter of the shaft 342 can be constant along the longitudinal length of the shaft 342. In a further example, the shaft 342 can include cutouts and/or hinges to accommodate the mass element 346 during delivery through the cannula bore 322.

The rotation mechanism 340 can also include a connection element 380 fixed to the shaft 342 and a mass element 346 fixed to the connection element 380. The connection element 380 can comprise a flexible member for connecting the mass element 346 to the shaft 342. Example connection elements 380 can include wires, threads, and/or sheets formed from a flexible material. Other example connection elements 380 can include pre-shaped highly elastic materials including, for example, Nitinol (NiTi) strips. The pre-shaped connection element 380 can be stressed in a deformed shape while within the cannula 420. Upon removal from the cannula 420, the pre-shaped connection element 380 can be restored to its original, undeformed shape.

As illustrated in FIGS. 12A-12D, the mass element 346 can have a round/spherical shape. In another example the mass element 346 can define any suitable shape including, for example, spherical, ellipsoid, cube, torus, cylindrical, or square, rectangular, or any other regular or irregular shape. The mass element 346 can include a cutting surface 352 on the perimeter or surface of the mass element 346 for dislocating material from a target area within the intervertebral disc (e.g., nucleus and/or annulus material) and/or cancellous bone. The cutting surface 352 can include sharp edges, a roughened surface, a blasted surface, and/or any other form of abrasive surface and/or feature formed on or attached to the mass element 346. For example, as illustrated in FIGS. 12A-12D, the mass element 346 can include a round/cylindrical mass having an abrasive surface for dislocating material from the target area. The mass element 346 can have a weight less than about 1 gram. In another example, the mass element 346 can have a weight of about 1 gram. In a further example, the mass element 346 can have a weight greater than about 1 gram. An example mass element 346 has uniform weight distribution. In another example, the mass distribution of the mass element 346 is concentrated at the cutting surface 352.

Figure 12A:
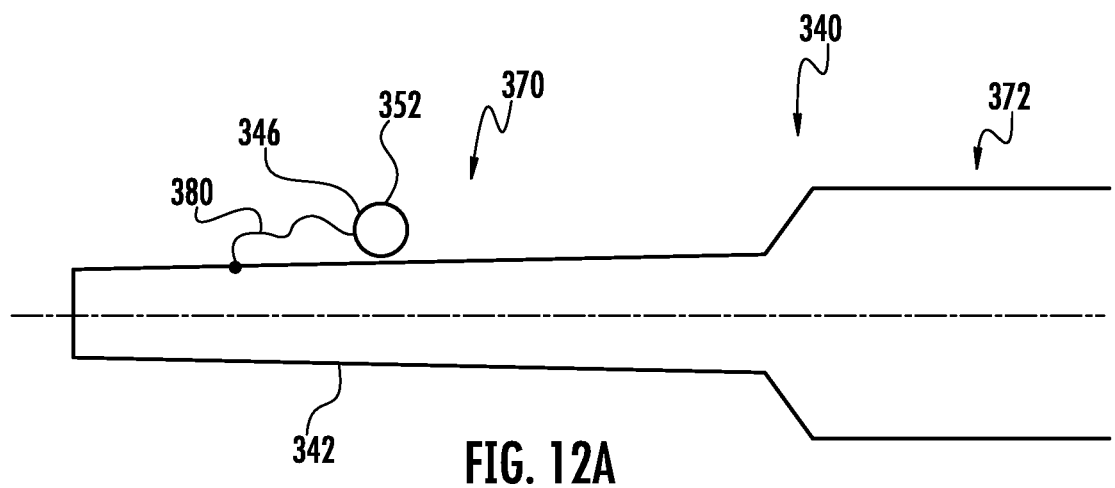
FIG. 12A is a partial side view of an example rotation mechanism.
Figure 12B:
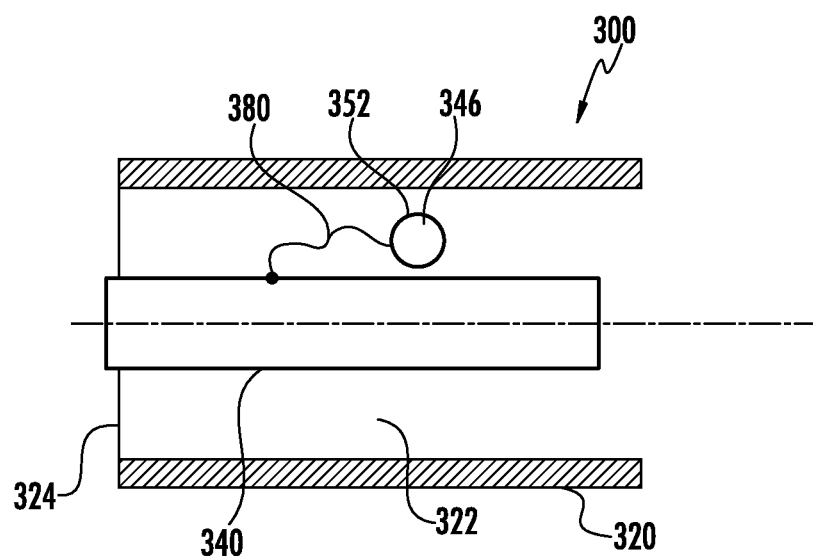
FIG. 12B is a partial side view of an example material removal instrument.

As illustrated in FIG. 12B, the mass element 346 can be attached to the shaft 342 via the connection element 380 such that the rotation mechanism 340 (shaft 342, connection element 380, mass element 346) can be inserted into the body/target area via the cannula 320.

Figure 12C:
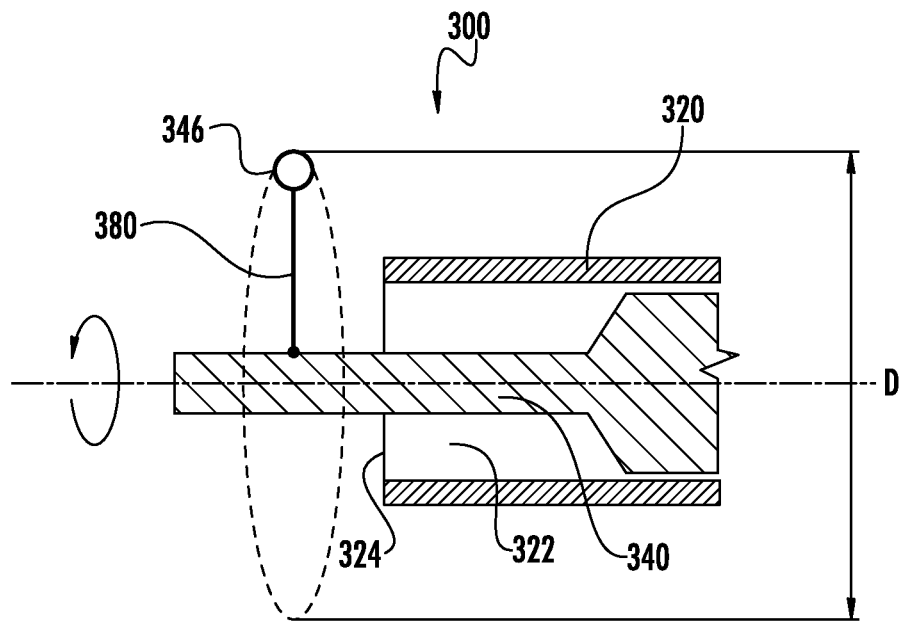
FIG. 12C is a partial side view of an example material removal instrument.
Figure 12D:
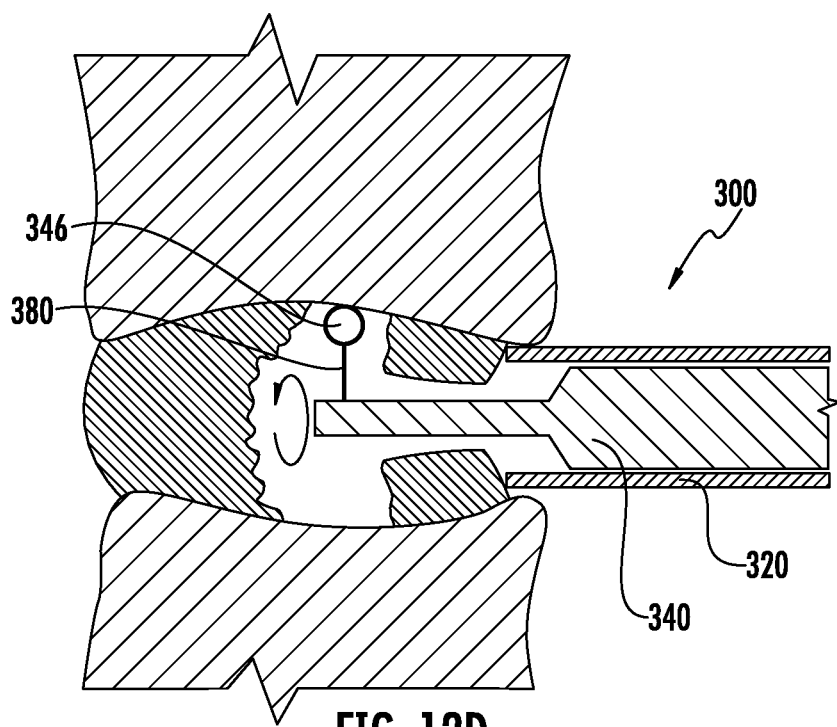
FIG. 12D is a posterior view of an example material removal instrument and vertebral bodies.

The rotation mechanism 340 can extend from an opening 324 in the cannula 320. Rotation of the shaft 342 can cause the connection element 380 and the mass element 346 to move in a direction away from the shaft 342. As illustrated in FIGS. 12C and 12D, during rotation of the shaft 342, the connection element 380 extends in a direction away from the longitudinal axis of the shaft 342. As the mass element 346 rotates around the longitudinal axis of the shaft 342, it impacts and dislocates material from the target area. The length of the connection element 380 and dimensions of the mass element 346 can be adjusted to define the maximum excavation diameter (D) created by rotation of the shaft 342. As illustrated in FIG. 12 C, the maximum excavation diameter (D) can be greater than the outer and/or inner diameter of the cannula 320.

Figure 13A:
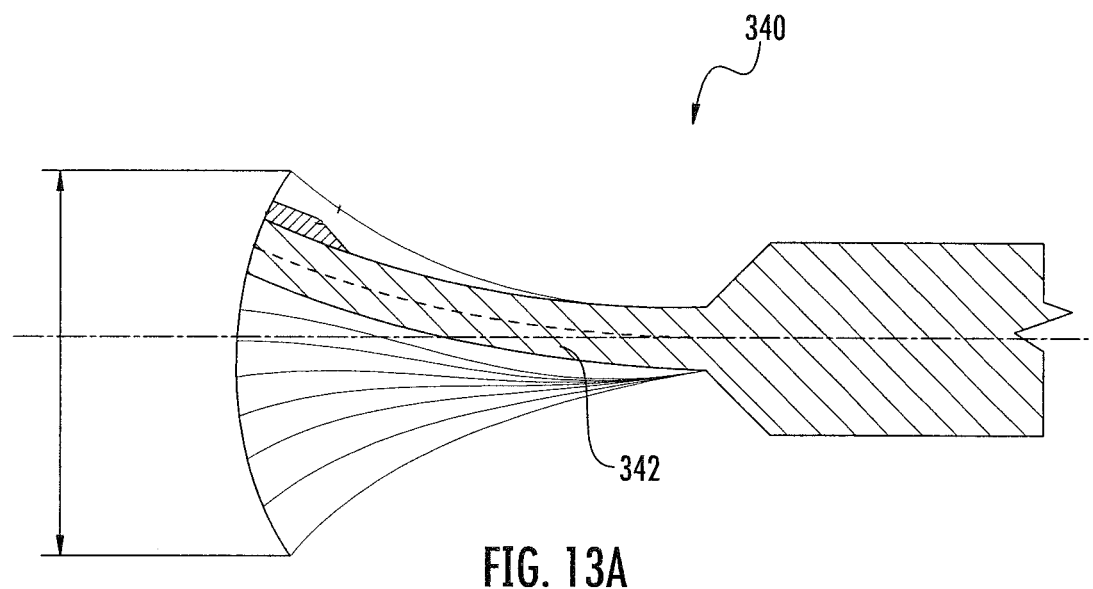
FIG. 13A is partial side view of an example rotation mechanism.
Figure 13B:
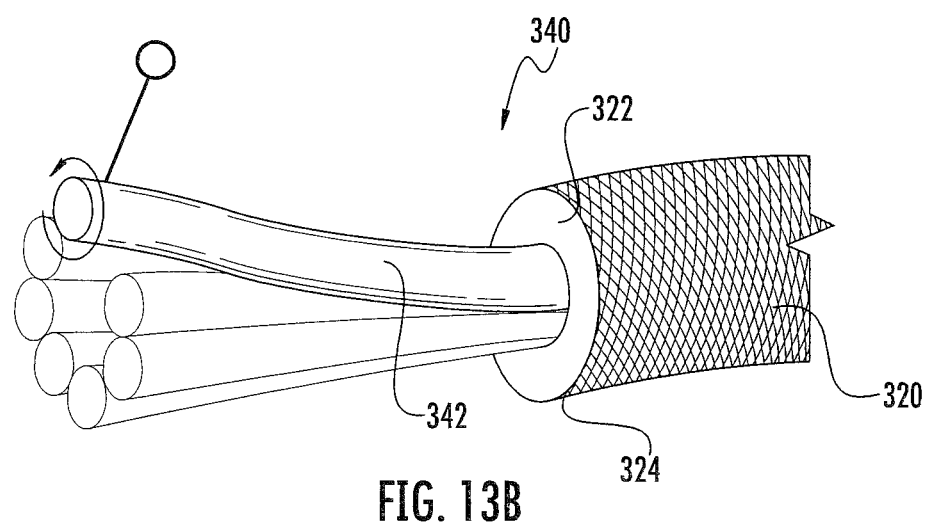
FIG. 13B is partial perspective view of an example rotation mechanism.
Figure 13C:
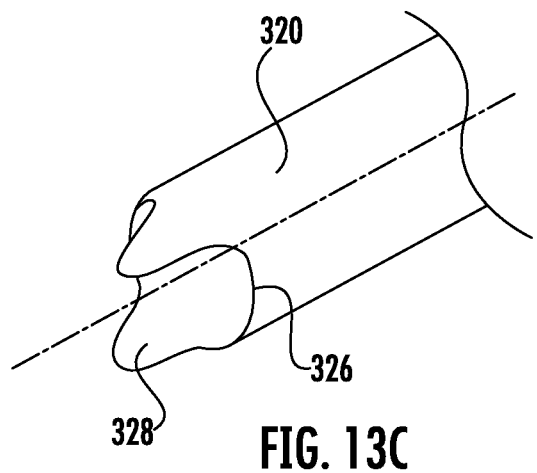
FIG. 13C is partial perspective view of an example cannula.
Figure 13D:
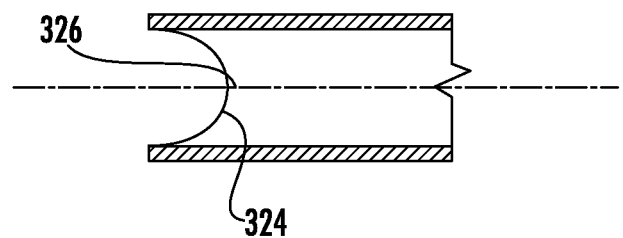
FIG. 13D is a partial side cross-section view of an example cannula.
Figure 13E:
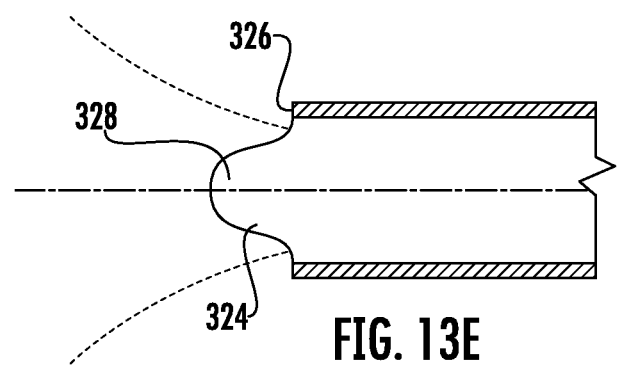
FIG. 13E is a partial top cross-section view of an example cannula.
Figure 13F:
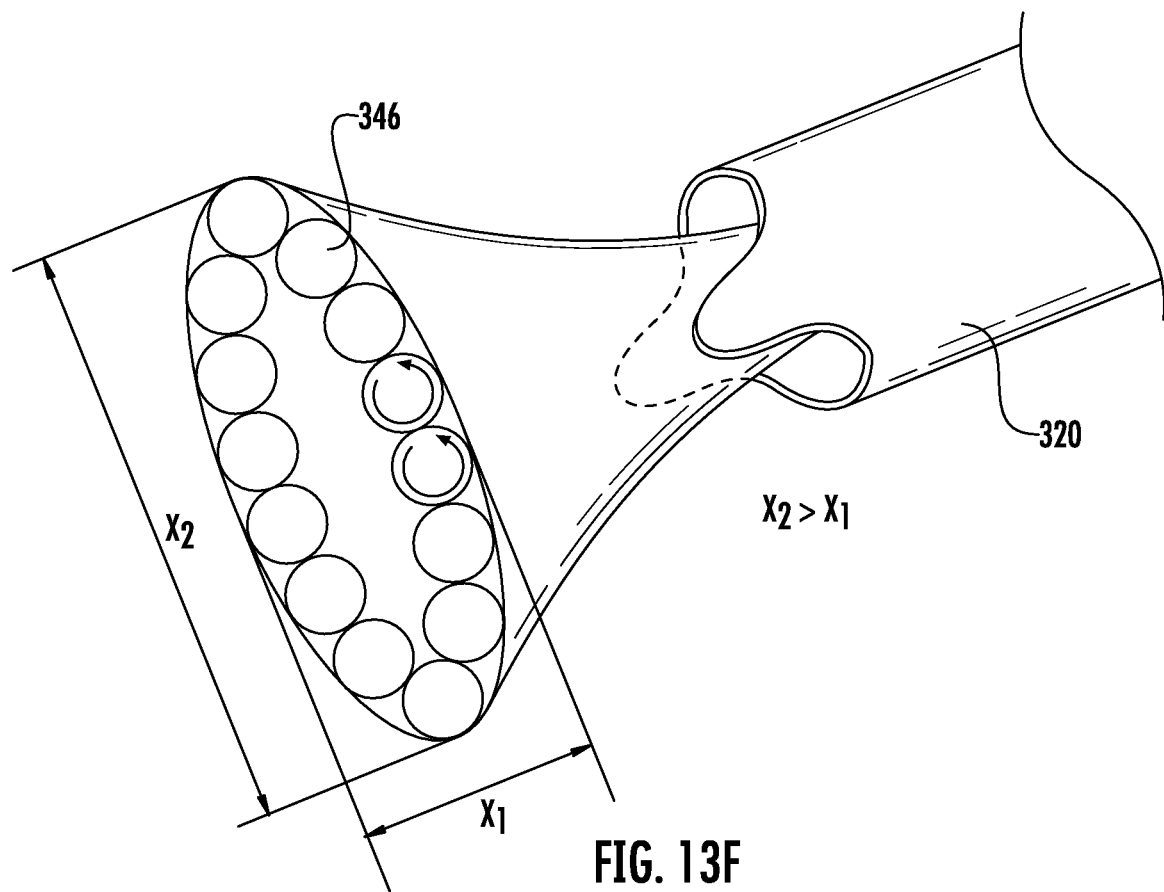
FIG. 13F is a partial perspective view of an example rotation mechanism and cannula.
Figure 14A:
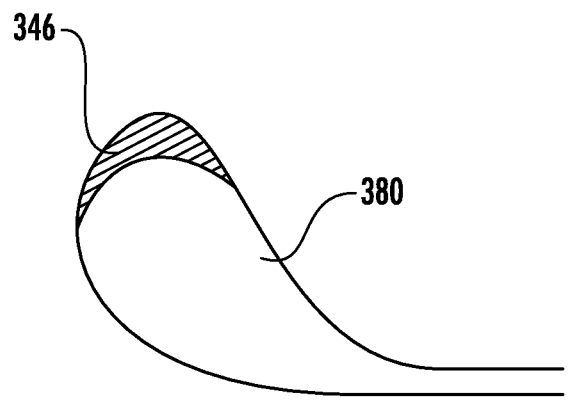
FIG. 14A is a side view of an example connection element and mass element.
Figure 14B:
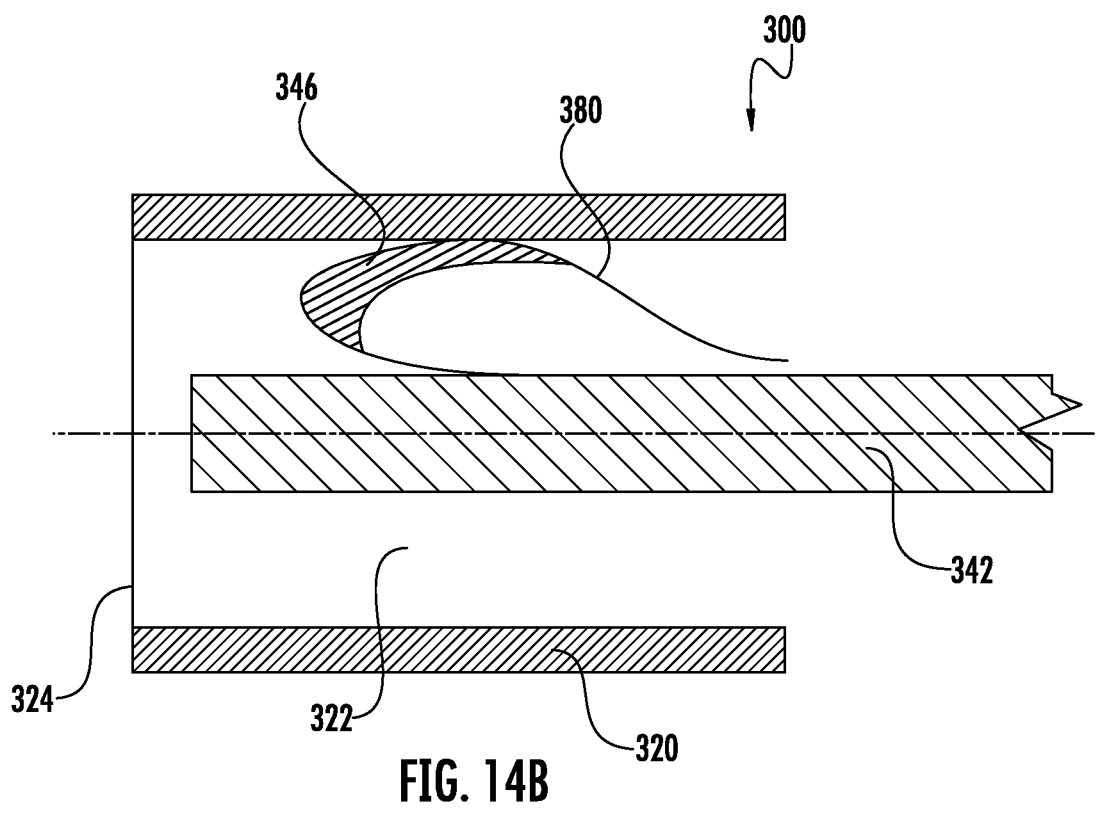
FIG. 14B is a partial side view of an example material removal instrument.
Figure 14C:
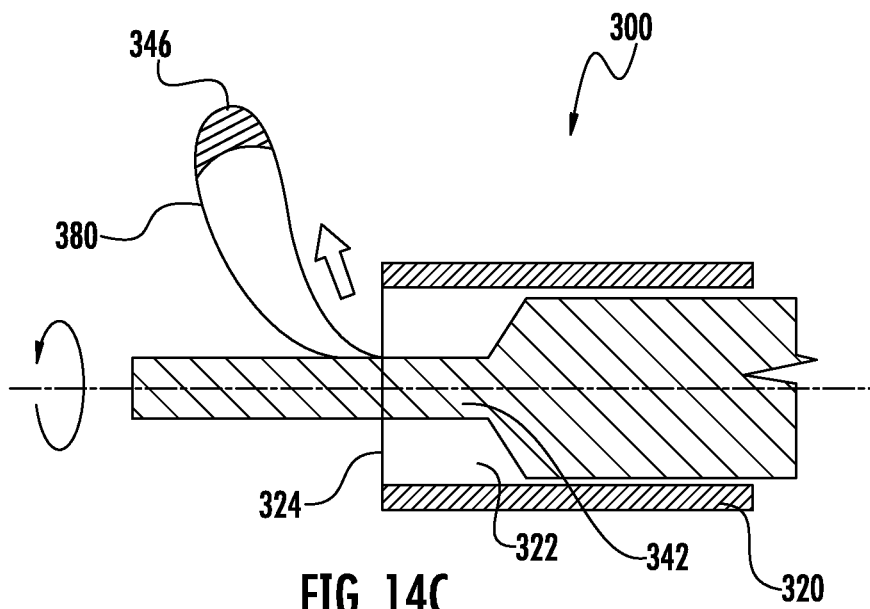
FIG. 14C is a partial side view of an example material removal instrument.
Figure 14D:
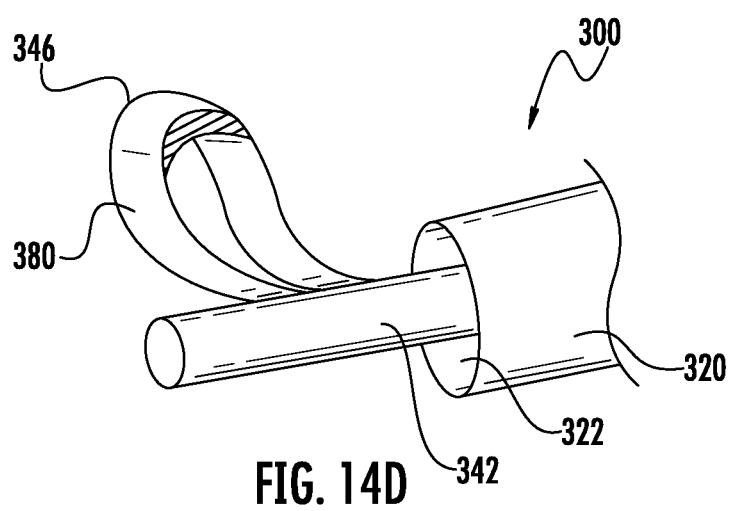
FIG. 14D is a partial perspective view of an example material removal instrument.

The shaft 342 can be constructed from a flexible material (e.g., polymers, Nitinol) or a rigid material. An example shaft 342 constructed from a stiff and/or rigid material can include structural modification (e.g., geometric cutouts or shapes) that provide an overall flexible behavior regarding cross forces. The example rotation mechanism illustrated in FIGS. 13A and 13B includes a shaft 342 constructed from a flexible material. An example shaft 342 constructed from a stiff and/or rigid material can include geometric cutouts or shapes that provide an overall flexible behavior regarding cross forces (e.g. spring). As provided in FIG. 13A, the mass element 346 can be attached directly to the flexible shaft 342 without the use of a connecting element 380. In the example rotation mechanism 340 illustrated in FIGS. 13A and 13B, the excentric center of mass of the shaft 342 and mass element 346 can result in an imbalance when rotating the shaft 342. If the surface of the elongated shaft 342 also includes a cutting surface 352 such that the elongated shaft 342 (in addition to the mass element 346) can impact and dislocate material, the imbalanced center of mass can create a cone shaped cavity at the target area.

Depending on the desired application and patient anatomy, it may be desirable to vary the shape of the cavity. When using a flexible shaft 342, the shape of the cavity can be varied by changing the shape of the cannula opening 324. For example, the shape of the opening 324 can be varied as illustrated in FIGS. 13C-13F. The opening 324 can include a recessed portion 326 and a protruding portion 328 where the shape of the opening defines the rotation/path of the flexible shaft 342 and the mass element 346. In particular, the recessed portion 326 permits the shaft 342 to rotate to a diameter ($X_1$) and the protruding portion permits the shaft 342 to rotate to a diameter ($X_2$), where $X_2$ is greater than $X_1$.

In another example material removal instrument 300 illustrated in FIGS. 14A-14D, the connection element 380 can include a flexible strip of material having a mass element 346 attached to a portion of the strip. In the example rotation mechanism 340, the mass element 346 is integrally formed on the connection element 380. For example, the mass element 346 can be formed at a folded portion of the connection element 380. The mass element 346 can be located at a position on the connection element 380 that defines the greatest distance from the longitudinal axis of the shaft 342 when the connection element 380 and mass element 346 are in a deployed position (e.g., when the shaft 342 is rotating and the connection element 380 is extended from the shaft 342). The lighter, thinner, and/or more flexible portions of the folded connection element 380 can be located between the mass element 346 and the shaft 342. It is also contemplated that the mass element 346 can be located at a position on the connection element 380 that defines the greatest distance from the longitudinal axis of the shaft 342 when the connection element 380 and mass element 346 are in an undeployed position. When the center of mass of the mass element 346 can also define the greatest distance from the longitudinal axis of the shaft 342 and the resulting force that moves the mass element 342 away from the rotation axis is higher. That is, applying Newton's second law (F=ma), the centripetal force (F) on the mass element 346 can be determined using the following formula $F = m\omega^2 r$, where m is the mass of the mass element 346, ω is the rotational speed of the mass element 346, and r is the radius of rotation (distance between the mass element 346 and the rotation axis).

Figure 15E:
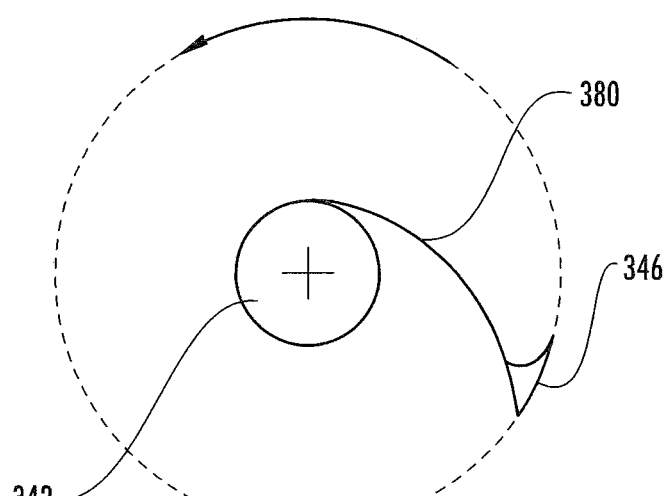
FIG. 15E is a partial end view of an example rotation mechanism.
Figure 15F:
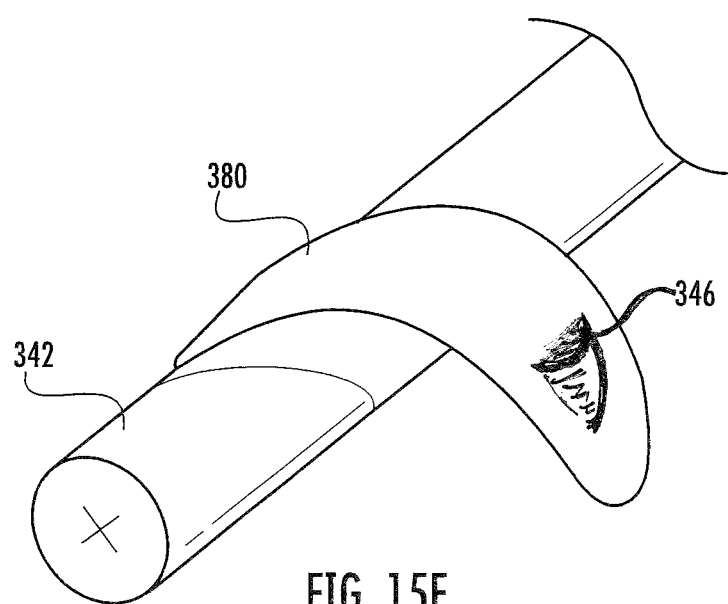
FIG. 15F is a partial perspective view of an example rotation mechanism.

Another example material removal instrument 300 is illustrated in FIGS. 15A and 15F. The connection element 380 is a flat strip of flexible material capable of being wrapped around the shaft 342. The mass element 346 can include a sharpened spike or other edge/projection formed on and/or fixed to the surface of the connection element 380. The connection element 380 is shown in an undeployed configuration in FIGS. 15B-15D. As the shaft 342 is rotated, centrifugal forces urge the connection element 380/mass element 346 outwards with regard to the rotation axis of the shaft 342, as illustrated in FIGS. 15E and 15F. Because the properties of the connection element 380 (width, thickness, material, pre-shaping, etc.) can alter the centrifugal forces on the mass element 346 and/or the rotational speed of the shaft 342, the excavation diameter of the cavity can be adjusted.

Figure 16B:
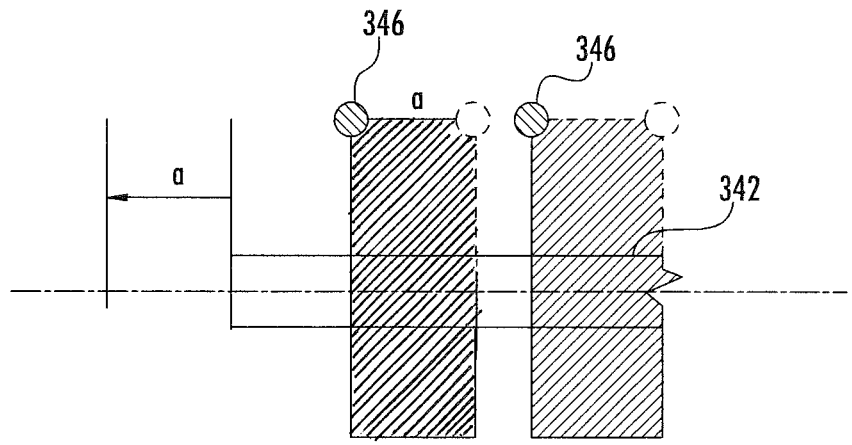
FIG. 16B is a side view of an example rotation mechanism.
Figure 16C:
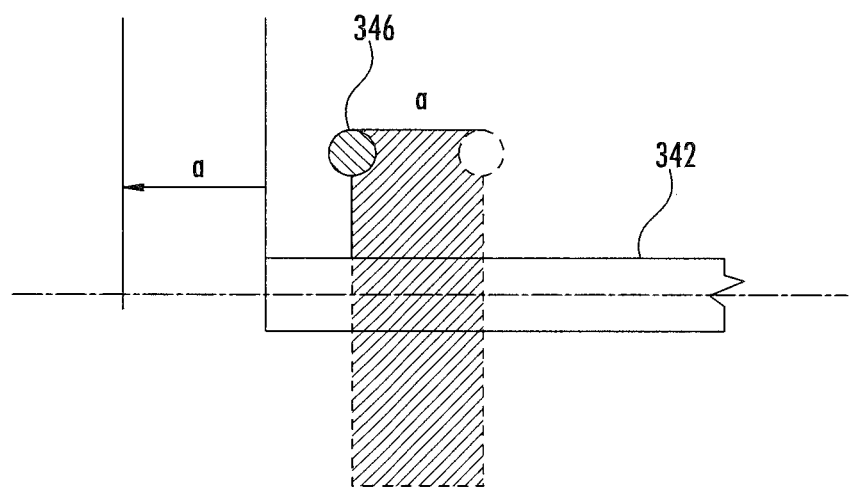
FIG. 16C is a side view of an example rotation mechanism.

Another example material removal instrument 300 is illustrated in FIGS. 16A and 16B. To increase the cutting performance of the rotation mechanism 340 (i.e., amount of cut or detached material per unit of time), the rotation mechanism 340 can including a plurality of mass elements 346. When only one mass element 346 is used, a disc-like cavity is created (see FIG. 16C). To enlarge the cavity, the rotation mechanism 340 must be moved in the axial direction (distance "a" in FIG. 16C), thereby creating a cylindrically-shaped cavity. When multiple mass elements 346 are used, the same amount of axial movement (distance "a" in FIG. 16B), results in larger cavity than the single mass element 346 cavity. Moreover, if a single mass element 346 detaches disc material at a certain rate (e.g., grams per second), multiple mass elements 346 can detach more disc material at a greater rate (assuming that the source of rotational energy driving the rotation mechanism 340 can maintain a constant turning speed).

As illustrated in FIG. 16A, mass elements 346 can be provided at shifted/offset locations along opposite sides of the length of the shaft 342. In another example (not shown), the mass elements 346/connection elements 380 can extend from the shaft 342 at mirrored positions along the length of the shaft 342. In another example illustrated in FIG. 16B, multiple mass elements 346 extend from one side of the shaft 342. In a further example, a plurality of mass elements 346 can extend from any location around the perimeter (diameter) of the shaft 342. The rotation mechanism 340 can include an even or odd number of mass elements 346. The mass of each of the mass elements 346 can vary, or the mass can be constant for each of the plurality of mass elements 346. The size and/or shape of each of the mass elements 346 and connection elements 380 can vary, or the size and/or shape can be constant for each of the plurality of mass elements 346.

The rotation mechanism 340 can be disposed within a cannula 320. The cannula 320 can be similar in form and function to cannula 120 and cannula 220, as outlined above. The cannula 320 can include a central bore (not shown) sized and configured to accommodate rotation of the rotation mechanism 340. The cannula 320 can also include an opening 324 providing access to the central bore 322. The opening 324 can be located on the cannula 320 such that the rotation mechanism 340 (including the mass elements 346) is provided access to the target area when the material removal instrument 300 is located within the patient. The cannula 320 can be constructed from a flexible material (e.g., polymers, Nitinol) or a rigid material. An example cannula 320 constructed from a stiff and/or rigid material can include structural modification (e.g., geometric cutouts or shapes) that provide an overall flexible behavior regarding cross forces.

In use, the material removal instrument 300 can remove bony material and/or disc material between adjacent vertebrae. As illustrated in FIG. 12B, the cannula 320 and rotation mechanism 340 can be provided into the disc/bone space in an undeployed configuration. The cannula opening 324 is proximate the target area within the disc/bony material. As provided in FIGS. 12C and 12D, the rotation mechanism 340 can be adjusted to extend from the cannula opening 324 at the target location. The rotation mechanism 340/shaft 342 can be operatively coupled to a source of rotation energy causing the rotation mechanism 340 rotate. An example rotation mechanism can rotate at speed raging from about 1,000 rpm to about 20,000 rpm. Centrifugal forces resulting from the rotation of the shaft 342 force the mass element 346 and the connection element 380 in a direction away from the axis of rotation (i.e., the longitudinal axis of the shaft 342). The rotation of the shaft 342 also causes the mass element 346 to rotate about the longitudinal axis of the shaft 342 at an angular velocity and in a generally circular trajectory. As the mass element 346 is rotated about the axis of the shaft 342, the inertia and trajectory of the mass element 346 cause the cutting surface 352 to contact and dislocate disc material from the target location. The required rotational speed can be determined based on the weight of the mass element 346 and the distance between the center of the mass element and the axis of rotation.

As illustrated in FIG. 12C, the rotating mass element 346 can define a diameter (D) of rotation that determines the size of the cavity. The diameter (D) can be defined by the length of the connection element 380 and the size of the mass element 346. The flexibility/resistance of the connection element 380 can also influence the diameter (D). For example, a flexible connection element 380 can fully expand into the disc space along the length of the connection element 380. In another example using a semi-flexible connection element 380, the resistance of the connection element 380 can resist full expansion during rotation. The length and/or flexibility of the connection element 380 and the size of the mass element 346 can be provided such that the diameter (D) of rotation is similar to the maximum disc height between superior and inferior vertebral bodies. Likewise, the length and/or flexibility of the connection element 380 and the size of the mass element 346 can be provided such that the diameter (D) of rotation is greater than the outer diameter of the cannula 320.

As illustrated in FIG. 12D, the shaft 342 can be moved in the axial direction to cause the mass element 346 to advance within the disc material and thereby remove additional material, enlarging the cavity. Likewise, the shaft 342 and/or cannula 320 can be moved in the lateral and/or vertical direction to remove to cause the mass element 346 to impact additional disc material and enlarge the cavity in the lateral and/or vertical directions.

FIGS. 17-18 provide partial side views of other example material removal instruments 400. The example material removal instrument 400 can include a cannula 420, a cutting element 446, and an inner element 480 attached to the cutting element 446. The cutting element 446 can be disposed within the cannula 420. The cannula 420 can be similar in form and function to cannula 120, cannula 220, and cannula 320, as outlined above. The cannula 420 can be constructed from a flexible or rigid material. The cannula 420 can include a central bore (not shown) sized and configured to accommodate the cutting element 446 and inner element (not shown). The cannula 420 can also include an opening 424 providing access to the central bore. The opening 424 can be located such that at least a portion of the cutting element 446 is provided access to the target area when the material removal instrument 400 is located within the patient.

Figure 17B:
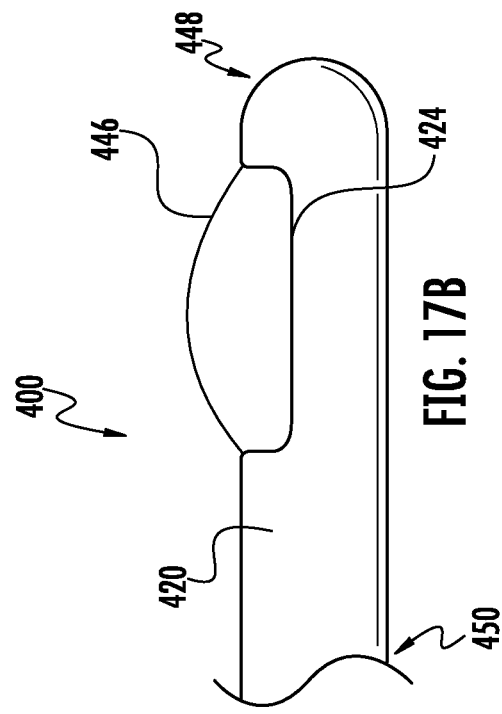
FIG. 17B is a partial side view of an example material removal instrument.
Figure 17D:
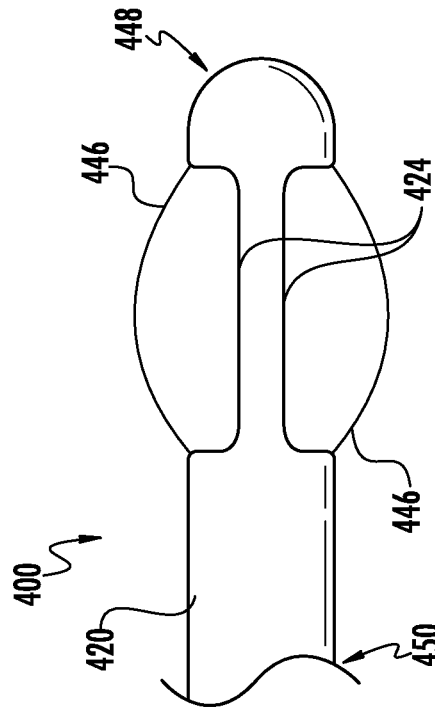
FIG. 17D is a partial side view of an example material removal instrument.
Figure 17A:
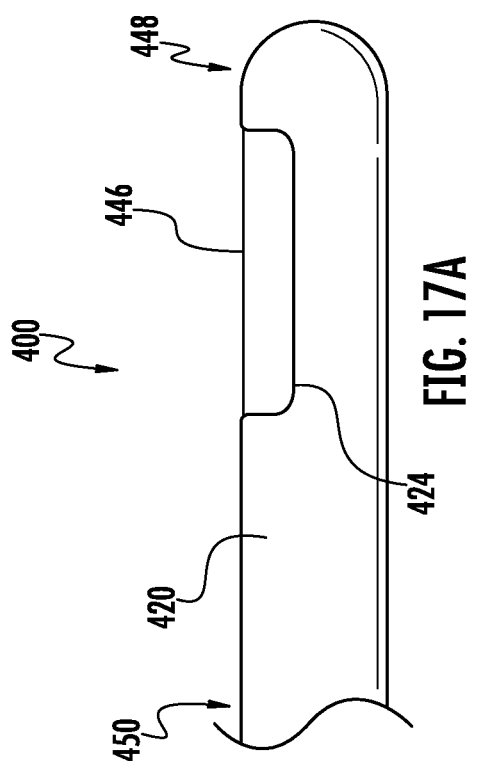
FIG. 17A is a partial side view of an example material removal instrument.
Figure 17C:
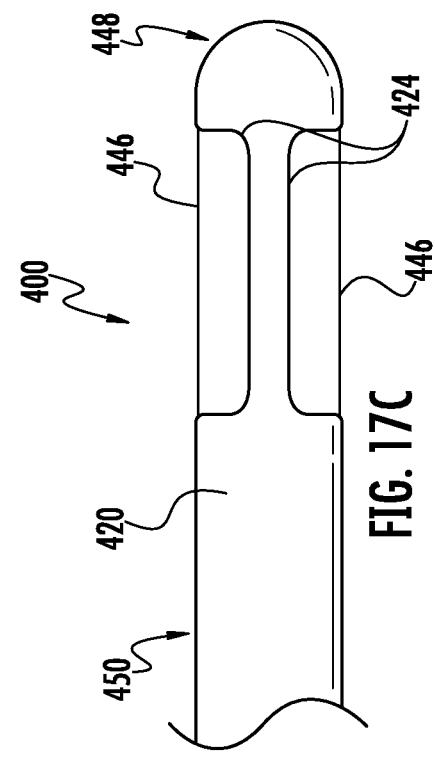
FIG. 17C is a partial side view of an example material removal instrument.
Figure 17E:
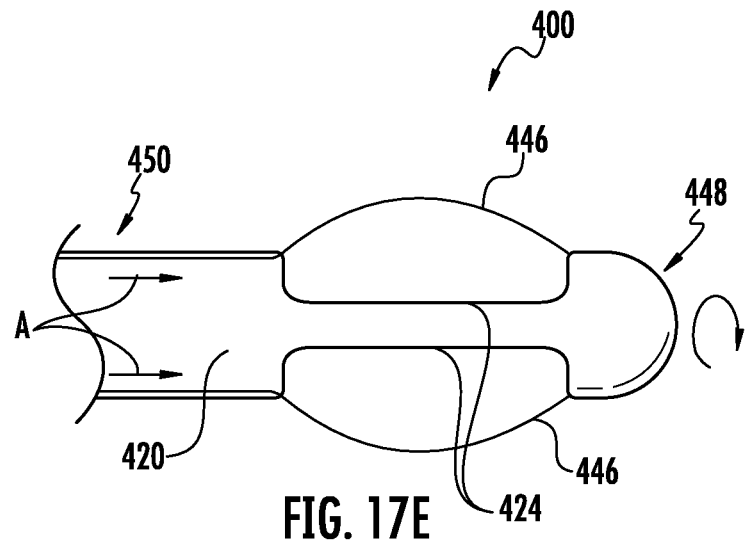
FIG. 17E is a partial side view of an example material removal instrument.
Figure 17F:
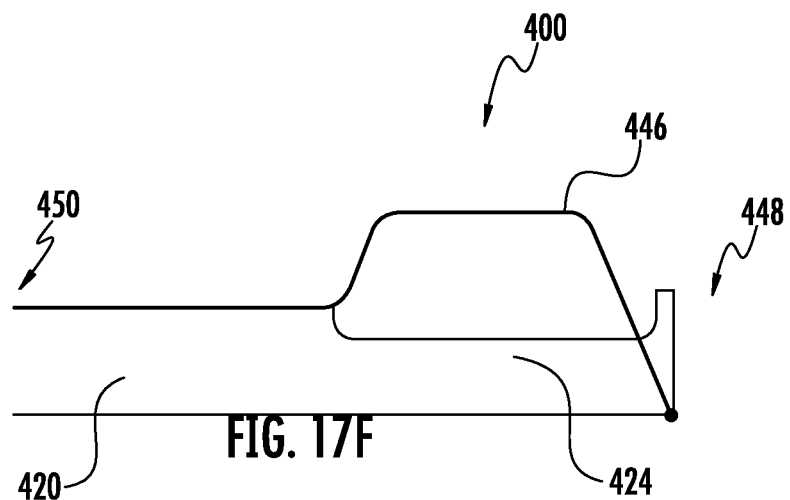
FIG. 17F is a partial side view of an example material removal instrument.

As illustrated in FIGS. 17A, 17B and 17F, the cannula 420 can include a single opening 424. In another example, the cannula 420 can include a plurality of openings 424 located around the around the outer surface of the cannula 420. For example, as illustrated in FIGS. 17C-17E, the cannula 420 can include two openings 424 provided on opposite sides of the cannula 420. The opening 424 can be located on a lateral surface of the cannula 420.

Figure 18A:
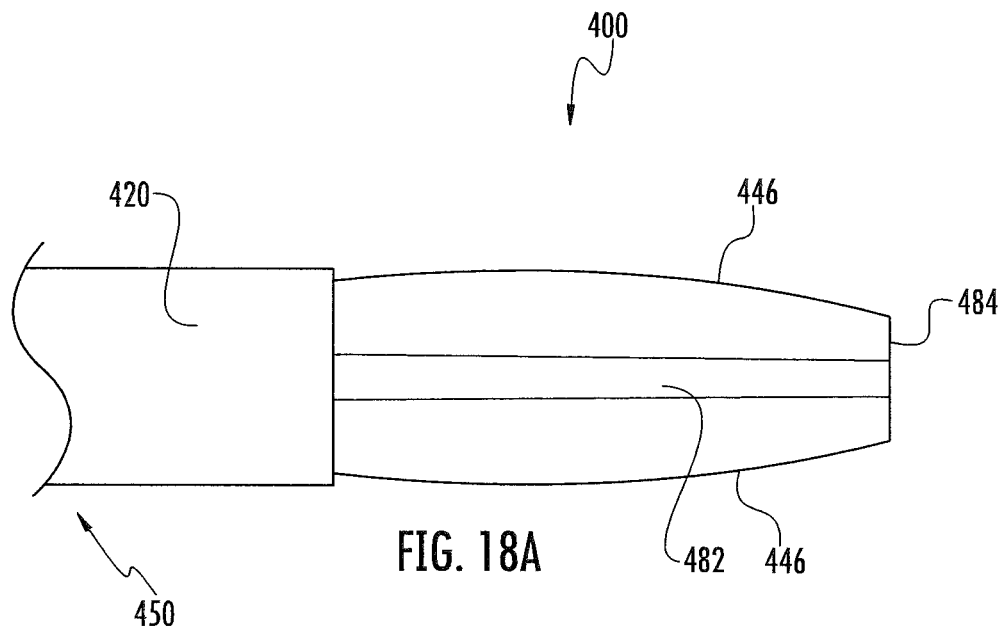
FIG. 18A is a partial side view of an example material removal instrument.
Figure 18B:
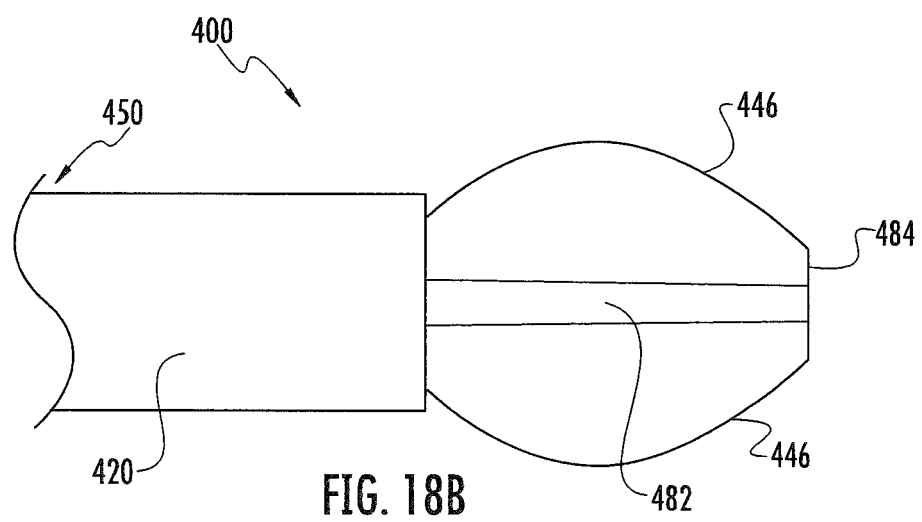
FIG. 18B is a partial side view of an example material removal instrument.
Figure 18C:
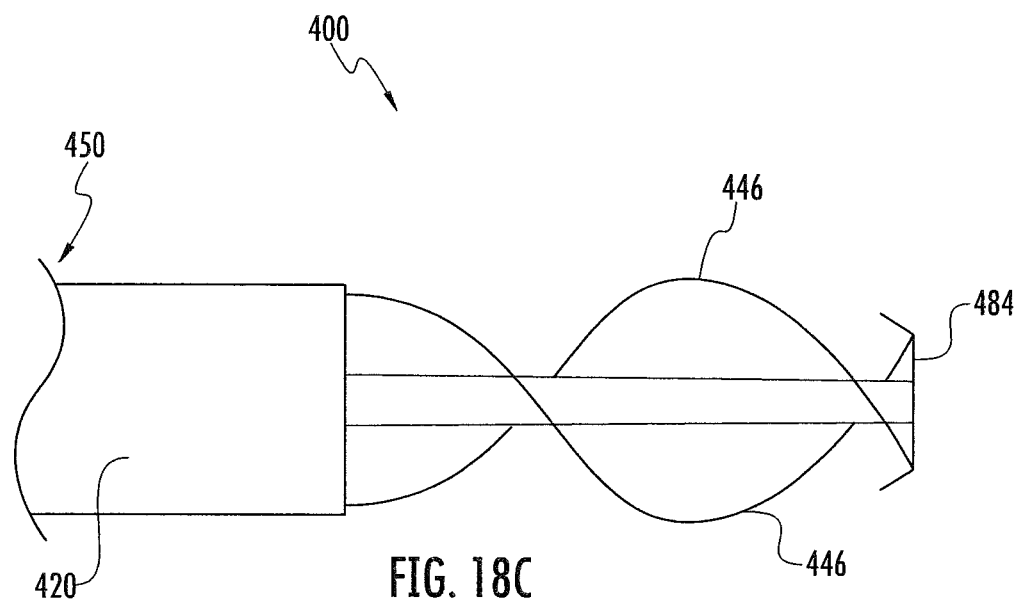
FIG. 18C is a partial side view of an example material removal instrument.
Figure 18D:
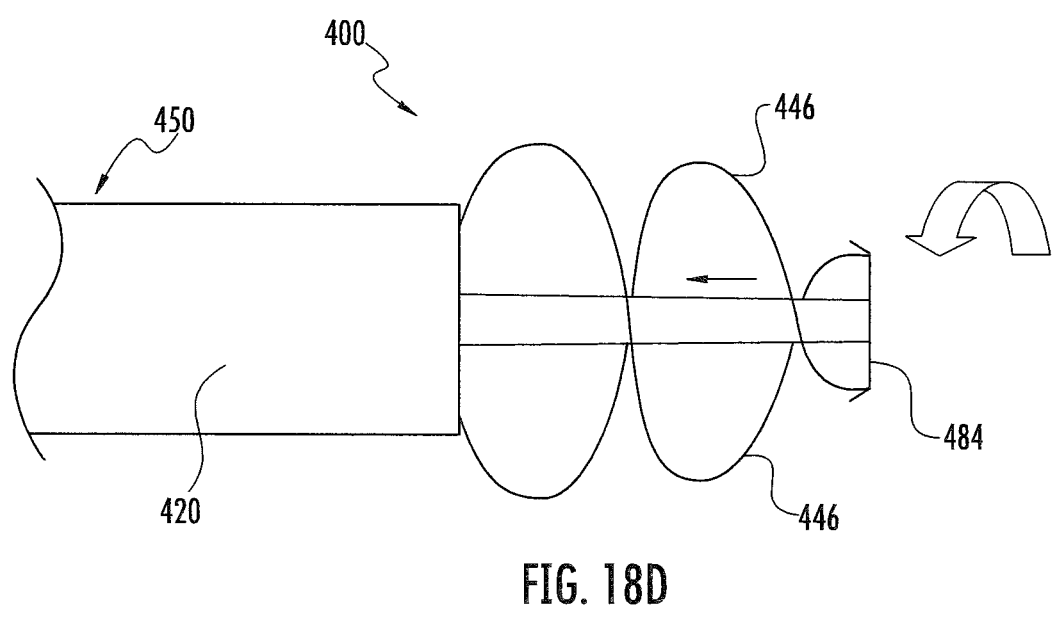
FIG. 18D is a partial side view of an example material removal instrument.

In another example illustrated in FIGS. 18A and 18B, the opening 424 can be located on the end surface at the distal end 448 of the cannula 420. The opening 424 can define any suitable shape including, for example, circular, elliptical, square, rectangular, or any other regular or irregular shape.

The cutting element 446 can include a flexible blade and/or wire. A portion of the cutting element 446 can be fixed to the inner element such that movement of the inner element expands the cutting element 446 radially through the cannula opening 424. The expanded cutting element 446 can define an outer diameter greater than the outer diameter of the cannula 420. For example, the expanded cutting element 446 can define an outer diameter greater than the outer diameter of the cannula 420 by about 1 mm to about 24 mm. That is, the cutting element 446 can expand radially from the outer surface of the cannula 420 from about 2 mm to about 12 mm.

In an example material removal instrument 400, movement of the inner element in the direction along the longitudinal axis of the cannula 420 applies a force on the cutting element 446 expanding the cutting element 446 radially through opening 424. In one example illustrated in FIGS. 17A-17E, the proximal end of the cutting element 446 can be fixed to the inner element such that movement of the inner element in a direction towards the distal end 448 (Arrows A in FIG. 17E) of the cannula 420 expands the cutting element 446 radially through the opening 424.

Figure 17G:
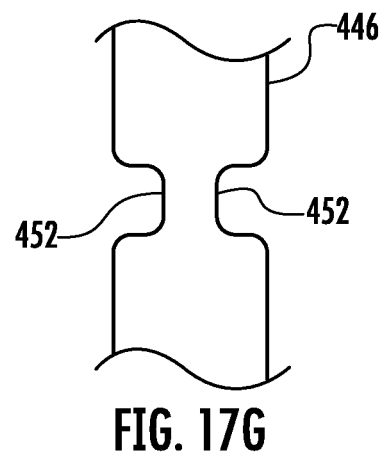
FIG. 17G is a partial top view of an example cutting element.

In another example illustrated in FIGS. 17F and 17G, radial expansion of the cutting 446 can be controlled by changing the geometry of the cutting element 446. For example, the profile of the cutting element 446 can be narrowed in the portions where deformation/radial expansion is desired. As illustrated in FIG. 17G, the profile of the cutting element 446 can be narrowed by including recesses 452 on the side portions of the cutting element 446. It is contemplated that the recesses 452 can have a square, curved, or any regular or irregular shape.

In another example illustrated in FIGS. 18A and 18B, the inner element includes a central shaft 482 and end cap 484. The proximal end of the cutting element 446 can be coupled to the cannula 420 and the distal end of the cutting element 446 can be coupled to the end cap 484. Movement of the central shaft 482 in a direction towards the proximal end 450 of the cannula 420 applies a force on the cutting element 446 expanding the cutting element 446 radially through opening 424. In a further example illustrated in FIGS. 18C and 18D, the central shaft 482 and/or end cap 484 can be rotated around the longitudinal axis of the central shaft 482. The proximal end of the cutting element 446 can be coupled to cannula 420 and the distal end of the cutting element 446 can be coupled to the end cap 484 such that rotation of the central shaft 482/end cap 484 causes the cutting element 446 to rotate around the central shaft 482 and form a helical cutting surface.

As outlined above, the cannula 420 and the elongated shaft 424 can both be constructed from a flexible material (or a material exhibiting flexible response). A cannula 420 and/or shaft 424 constructed from a flexible material allows for steering when accessing the target area. Flexibility can also increase the range of motion of the material removal instrument 400.

In use, the material removal instrument 400 can remove bony material and/or disc material between adjacent vertebrae. The cannula 420, including the cutting element 446, can be provided into the disc/bone space such that the cannula opening 424 is proximate the target area. Once positioned at the target area, the cutting element 446 can be expanded radially from the opening 424. The cannula 420 can be operatively coupled to a source of rotation energy. Rotation of the cannula 420 causes the expanded cutting element 446 to contact and dislocate disc material at the target location and create a cavity within the disc space. The cavity can be expanded by moving the rotating cannula 420/cutting element 446 axially, laterally, and/or vertically within the disc space.

It should be noted that specific features of the various embodiments disclosed herein can be performed manually by user-applied forces or, alternately, utilizing specialized motors/power sources. For example, rotation of the various components of the rotation mechanism 100, 200, 300 and/or cannula 420 can be performed manually by a surgeon. Conversely, rotation of the various components of the rotation mechanism 100, 200, 300 and/or cannula 420 can be performed by motorized components that may utilize, in certain implementations, microprocessors or other guidance systems to coordinate the rotation speed and location of the cutting surface to optimally form the cavity within the target body.

It is contemplated that each of the rotation mechanisms 140, 240, 340 and cannula 420 can each include a central bore. The central bore can be used to provide irrigation to the cutting area. The central bore can be operatively coupled to an irrigation source for providing irrigation to bore openings provided at the distal ends of the rotation mechanisms 140, 240, 340 and/or cannula 420. The irrigation can be provided to dissipate heat generated between the rotation mechanism 140, 240, 340 and/or cannula 420 and the target area. The irrigation can also dissipate heat generated between the rotation mechanism 140, 240, 340 and/or cannula 420 and the cannula 120, 220, 320 and/or the introducer cannula 102. The irrigation can also prevent dislocated material (e.g., soft tissue, bone, blood, or other interstitial fluid/materials) from adhering to the blade, projections, threads, cutting surface, mass element, cutting surface, and/or inner surface of the cannula bore and/or introducer cannual included in any one of the material removal instruments 100, 200, 300, 400. The irrigation can also aid the flow of the dislocated material from the target area through the cannula 120, 220, 320, 420. It is further contemplated that the bore included in each of the rotation mechanisms 140, 240, 340 and cannula 420 can be sized and configured to receive a guide wire to direct placement of the rotation mechanism 140, 240, 340/cannula 420. An example guide wire can include a Kirschner wire (K-wire).

It is also contemplated that the cannula 120, 220, 320, 420 for each of the described material removal instruments 100, 200, 300, 400 can exhibit flexible behavior. All or a portion of the cannula 120, 220, 320, 420 may be constructed from a rigid or flexible material. Flexibility can be achieved based on the material properties of the cannula 120, 220, 320, 420, structural properties and/or modifications to the cannula 120, 220, 320, 420, and/or a linkage with another portion of the material removal instrument. Similarly, all or a portion of the rotation mechanisms 140, 240, 340 for each of the described material removal instruments 100, 200, 300, 400 can also exhibit flexible behavior. In particular, the elongated shaft 142, 242, 342 may be constructed from a rigid or flexible material. Flexibility can be achieved based on the material properties of the rotation mechanism 140, 240, 340/elongated shaft 142, 242, 342, structural properties and/or modifications to the rotation mechanism 140, 240, 340/elongated shaft 142, 242, 342, and/or a linkage with another portion of the material removal instrument 100, 200, 300, 400. Flexibility of the cannula 120, 220, 320, 420 and/or the rotation mechanism 140, 240, 340 can be used to provide steering/directional control when accessing the target area and during removal of tissue.

One or more components of the material removal instrument 100, 200, 300, 400 may be made from any biocompatible material known including, for example, metals such as titanium, titanium alloys, stainless steel and cobalt chromium, cobalt chromium molybdenum (CoCrMo), or other metals. Other materials include, for example, composites, polymers, or ceramics. In one example, one or more components of the material removal instrument 100, 200, 300, 400 can be constructed from a radiopaque material including, for example, stainless steel such as 17-4PH stainless steel. Likewise, one or more components described herein can be constructed from a radiolucent material to enhance visibility of the assembly during radiographic imaging. Example radiolucent materials can include "life science" grade PEEK (Ketron 450G PEEK). Life science grade PEEK can improve wear and abrasion characteristics as well as provide high yield strength. A coating may be added or applied to the various components described herein to improve physical or chemical properties, such as a plasma-sprayed titanium coating or Hydroxypatite. Moreover, skilled artisans will also appreciate that the various components herein described can be constructed with any dimensions desirable for implantation and cavity creation.

While the foregoing description and drawings represent the preferred embodiment of the present invention, it will be understood that various additions, modifications, combinations and/or substitutions may be made therein without departing from the spirit and scope of the present invention as defined in the accompanying claims. In particular, it will be clear to those skilled in the art that the present invention may be embodied in other specific forms, structures, arrangements, proportions, and with other elements, materials, and components, without departing from the spirit or essential characteristics thereof. One skilled in the art will appreciate that the invention may be used with many modifications of structure, arrangement, proportions, materials, and components and otherwise, used in the practice of the invention, which are particularly adapted to specific environments and operative requirements without departing from the principles of the present invention. In addition, features described herein may be used singularly or in combination with other features. The presently disclosed embodiments are, therefore, to be considered in all respects as illustrative and not restrictive, the scope of the invention being indicated by the appended claims and not limited to the foregoing description.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention, as defined by the following claims.

What is claimed is:

1. A material removal instrument, comprising:
a cannula, and
a rotation mechanism disposed at least partially within the cannula, the rotation mechanism including:
an elongated cylindrical shaft having a central bore, a longitudinal axis, and a shaft opening at a distal end of the elongated cylindrical shaft providing fluid communication between the shaft opening and the central bore;
a blade extending distal of the shaft opening such that the shaft opening provides a throughhole for fluid communication between the central bore and the blade, where a portion of the blade extends from the distal end of the elongated cylindrical shaft and forms a surface having two generally parallel longitudinally extending edges that rotate around the longitudinal axis of the cylindrical shaft,
wherein the rotation mechanism is rotatable within the cannula to cause the blade to dislocate material from a target area, and
wherein the blade comprises a longitudinal axis that is coaxial with the longitudinal axis of the cylindrical shaft when the blade is disposed outside the cannula.

2. The material removal instrument of claim 1, wherein the cannula includes a central cannula bore and a cannula opening at a distal end of the cannula, the cannula opening located on an end wall of the cannula and providing fluid communication between the cannula opening and the cannula bore,
wherein the rotation mechanism is sized and configured to be received within the cannula bore,
wherein the rotation mechanism is rotatable within the cannula to cause the blade to dislocate material from the target area,
wherein the dislocated material is drawn from the target area through the cannula bore.

3. The material removal instrument of claim 1, wherein the rotation mechanism further includes a projection extending from an outer surface of the elongated cylindrical shaft, the projection forming a helical-shaped surface extending around the elongated cylindrical shaft of the rotation mechanism,
wherein a height of the projection is less than a diameter of a central cannula bore such that the rotation mechanism can rotate freely within the central cannula bore,
wherein when the rotation mechanism is rotated within the central cannula bore the projection acts as a screw pump for moving dislocated material through the central cannula bore.

4. The material removal instrument of claim 1, wherein the blade extends in a radial direction from an outer surface of the elongated cylindrical shaft, the blade extending along a length of the shaft in a longitudinal direction from the distal end of the elongated cylindrical shaft towards a proximal end of the elongated cylindrical shaft.

5. The material removal instrument of claim 1, wherein a first portion of the blade extends in a radial direction from a first side of an outer surface of the elongated cylindrical shaft and a second portion of the blade extends from the outer surface of the elongated cylindrical shaft along a second side of the outer surface opposite the first side of the outer surface and the first portion of the blade.

6. The material removal instrument of claim 3, wherein the blade extends in a radial direction from the outer surface of the elongated cylindrical shaft between a distal end of the elongated cylindrical shaft and the projection.

7. The material removal instrument of claim 1, wherein the surface of the blade defines a generally rectangular shape forming a helical surface extending around the longitudinal axis of the cylindrical shaft.

8. The material removal instrument of claim 7, wherein a height defined by the diameter of the helical surface is generally constant during rotation.

9. The material removal instrument of claim 1, wherein a distal end edge of the blade extends perpendicular to the longitudinal axis of the elongated cylindrical shaft.

10. The material removal instrument of claim 1, wherein the blade includes a cutting surface provided on each longitudinally extending edge of the blade.

11. The material removal instrument of claim 10, wherein each of the cutting surfaces include an angular recessed surface extending between the planar surface of the blade and the corresponding longitudinally extending edge.

12. The material removal instrument of claim 10, wherein each of the cutting surfaces includes a curved recessed surface extending between the planar surface of the blade and the corresponding longitudinally extending edge.

13. The material removal instrument of claim 10, wherein the cutting surfaces include a first and second cutting surface,
wherein the longitudinally extending edges include a first and second longitudinally extending edge,
wherein the first cutting surface is provided at the first longitudinally extending edge and the second cutting surface is provided at the second longitudinally extending edge,
wherein the first and second cutting surfaces are provided on opposite sides of the surface of the blade.

14. The material removal instrument of claim 10, wherein the cutting surface includes a plurality of grooves extending from the longitudinally extending edge of the blade in a direction towards the longitudinal axis of the elongated cylindrical shaft.

15. The material removal instrument of claim 10, wherein the blade includes a cutting surface provided on each longitudinally extending edge of the blade,
wherein each of the cutting surfaces is provided on opposite sides of the surface of the blade,
wherein each of the cutting surfaces include an angular recessed cutting surface extending between the surface of the blade and the corresponding longitudinally extending edge, the recessed cutting surfaces including a leading surface adjacent the longitudinally extending edge and a trailing surface adjacent the surface of the blade,
wherein the plurality of grooves extend from the longitudinally extending edge of the blade and the leading surface of the recessed cutting surface.

16. The material removal instrument of claim 1, wherein the central bore of the rotation mechanism is operatively coupled to an irrigation source,
wherein the central bore of the rotation mechanism is sized and configured to receive a guide wire,
wherein a proximal end of the rotation mechanism is operatively coupled to a source of rotational energy.

17. A material removal instrument, comprising:
a rotation mechanism disposed at least partially within a cannula, the rotation mechanism including:
an elongated cylindrical shaft having a central bore, a longitudinal axis, and a shaft opening at a distal end of the elongated cylindrical shaft providing fluid communication between the shaft opening and the central bore;
a blade extending distal of the shaft opening such that the shaft opening provides a throughhole for fluid communication between the central bore and the blade, where a portion of the blade extends from the distal end of the elongated cylindrical shaft and forms a surface having two generally parallel longitudinally extending edges that rotate around the longitudinal axis of the cylindrical shaft wherein the rotation mechanism is rotatable within the cannula to cause the blade to dislocate material from a target area and
wherein the blade comprises a longitudinal axis that is coaxial with the longitudinal axis of the cylindrical shaft when the blade is disposed outside the cannula.

18. The material removal instrument of claim 17, wherein the blade extends in a radial direction from an outer surface of the elongated cylindrical shaft, the blade extending along a length of the shaft in a longitudinal direction from the distal end of the elongated cylindrical shaft towards a proximal end of the elongated cylindrical shaft.

19. The material removal instrument of claim 17, wherein a first portion of the blade extends in a radial direction from a first side of an outer surface of the elongated cylindrical shaft and a second portion of the blade extends from the outer surface of the elongated cylindrical shaft along a second side of the outer surface opposite the first side of the outer surface and the first portion of the blade.

20. The material removal instrument of claim 17, wherein the blade includes a cutting surface provided on each longitudinally extending edge of the blade,
wherein each of the cutting surfaces is provided on opposite sides of the planar surface of the blade,
wherein each of the cutting surfaces include an angular recessed cutting surface extending between the surface of the blade and the corresponding longitudinally extending edge, the recessed cutting surfaces including a leading surface adjacent the longitudinally extending edge and a trailing surface adjacent the planar surface of the blade,
wherein the plurality of grooves extend from the longitudinally extending edge of the blade and the leading surface of the recessed cutting surface.

* * * * *